(12) United States Patent
Sun et al.

(10) Patent No.: US 7,399,597 B2
(45) Date of Patent: Jul. 15, 2008

(54) **EPITOPE IDENTIFICATION AND MODIFICATION FOR REDUCED ALLERGENIC ACTIVITY IN PROTEINS T

OTHER PUBLICATIONS

Oommen A., et al., "Identification of IgE-binding epitopes of the Brazil nut 2S albumin allergen," *J. Allergy Clin. Immunol.* 105 suppl., 134 (2000).

Pastorello E.A., et al., "Sensitization to the major allergen of Brazil nut is correlated with the clinical expression of allergy," *J. Allergy Clin. Immunol.* 102, 1021-1027 (1998).

Payne P.I., "Breeding for protein quantity and protein quality in seed crops," In *Seed Proteins* (Ed. Daussant J., Mosse J. & Vaughan J.) 223-253 (*Academic Press Inc.*, London, 1983).

Reese G., et al., "Characterization and identification of allergen epitopes: recombinant peptide libraries and synthetic, overlapping peptides," *J. Chromatogr. B Biomed. Sci. Appl.* 756, 157-163 (2001).

Sen, M., et al., "Protein structure plays a critical role in peanut allergen stability and may determine immunodominant IgE-binding epitopes," *J. Immunol.* 169, 882-887 (2002).

Sun S.S.M, et al., "Properties, biosynthesis and processing of a sulfur-rich protein in Brazil nut (*Bertholletia excelsa* H.B.K.)," *Eur J Biochem.* 162, 477-483 (1987).

* cited by examiner

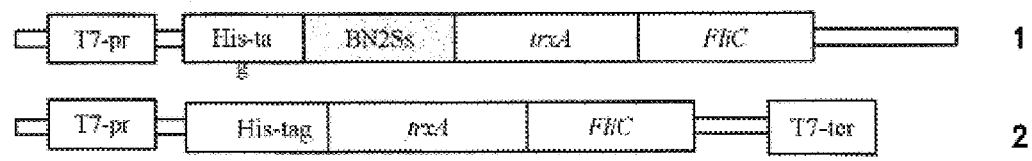
FIG. 1A
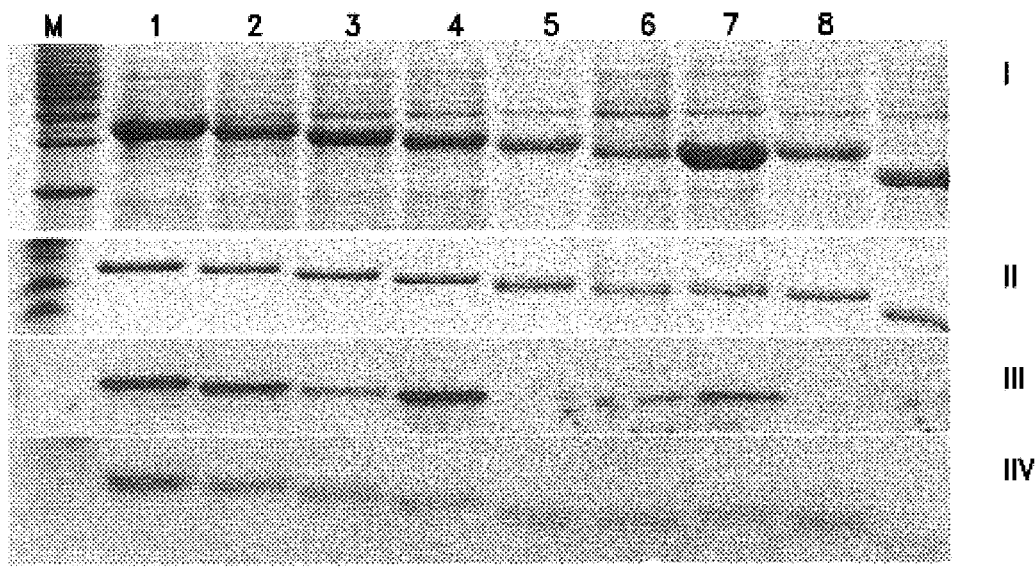
FIG. 1B
FIG. 1C

FIG. 2

The center region of the large subunit
(SEQ ID NO: 155)
```
GLRMMMMRMQQEEMQ PRG EQMRRMMR B0
       RMQQEEMQ PRG EQMRRMMR B2
         QQEEMQ PRG EQMRRMMR B3
            EMQ PRG EQMRRMMR B4
                PRG EQMRRMMR B5
                    EQMRRMMR B6
```

The center region of the large subunit
(SEQ ID NO: 156)
```
LAENIP SRC NLSPMRCPMGGSIAGF C0
   NIP SRC NLSPMRCPMGGSIAGF C1
       SRC NLSPMRCPMGGSIAGF C2
           NLSPMRCPMGGSIAGF C3
              PMRCPMGGSIAGF C4
                   GGSIAGF C6
```

The N-terminal region of the large subunit
(SEQ ID NO: 157)
```
PRRGMEPHSECCEQLEG MDESCRCE A0
   GMEPHSECCEQLEG MDESCRCE A1
      PHSECCEQLEG MDESCRCE A2
         SECCEQLEG MDESCRCE A3
               LEG MDESCRCE A5
                   MDESCRCE A6
```

The centre region of the large subunit
(SEQ ID NO: 158)
```
GLRMMMMRMQQE EMQ PRGEQMRRMMR B0
      MRMQQE EMQ PRGEQMRRMMR B2
         QQE EMQ PRGEQMRRMMR B3
             EMQ PRGEQMRRMMR B4
                 PRGEQMRRMMR B5
                    EQMRRMMR B6
```

tHE C-terminal region of the large subunit
(SEQ ID NO: 159)
```
LAENIPSCNLS PMRCPM GGSIAGF C0
   NIPSCNLS PMRCPM GGSIAGF C1
      SCNLS PMRCPM GGSIAGF C2
        NLS PMRCPM GGSIAGF C3
            PMRCPM GGSIAGF C4
                   GGSIAGF C6
```

The small subunit with the internal processed fragment
(SEQ ID NO: 160)
```
QEECREQMQRQQMLSHCRM YMR QQMMEESPYQTM S0
           LSHCRM YMR QQMMEESPYQTM S1
              CRM YMR QQMMEESPYQTM S2
                  YMR QQMMEESPYQTM S3
                      QQMMEESPYQTM S4

BNMRP 12 KD precursor

```
            Small Subunit                                              Large Subunit
      S0         S1              L1              L2             L3             L4             L5      L6
QEECREQMQRQQMLSHCRMYMRQQMEESPYQTMPRRGMEPHMSECCEQLEGMDESCRCEGLRMMMMRQQEEMQPRGEQMRRMMRLAENIPSRCNLSPMRCPMGGSIAGF
1              20              40              60             80                                   100
                                                                                          (SEQ ID NO: 161)

QEECREQMQ 1
  CREQMQRQQ 2
    QMQRQQMLS 3
      RQQMLSHCR 4
       QQMLSHCR 5
         LSHCRMYM 6
          CRMYMRQQ 7
            YMRQQMEE 8
             QQMEESPY 9
              EESPYQTM 10
                  PRRGMEPH 11
                   GMEPHMSE 12
                    PHMSECCE 13
                     SECCEQLE 14
                      CEQLEGMD 15
                       LEGMDESC 16
                        MDESCRCE 17
                         SCRCEGLRMM 18
```

BNMRP 12 KD precursor

```
  Small Subunit                                                    Large Subunit
   S0     S1              L1              L2             L3              L4             L5              L6
QEECREQMQRQQMLSHCRMYMRQQMEESPYQTMPRRGMEPHMSECCEQLEGMDESCRCEGLRMMMRMQQEEMQPRGEQMRRMRLAENIPSRCNLSPMRCPMGGSIAGF
1                   20              40             60              80             100
                                                                                                  (SEQ ID NO: 161)

GLRMMMR 19
                                                     MMMRMQQ 20
                                                      MRMQQEEM 21
                                                       QQEEMQPR 22
                                                        EMQPRGEQ 23
                                                         PRGEQMRR 24
                                                          EQMRRMR 25
                                                           RRMRLAEN 26
                                                            LAENIPS 27
                                                             NIPSRCN 28
                                                              SRCNLSP 29
                                                               NLSPMRC 30
                                                                PMRCPMG 31
                                                                 PMRCPMGGSI 32
                                                                     GGSIAGF 33
```

BNMRP 12 KD precursor

Small Subunit | Large Subunit

QEECREQMRQQMLSHCRMYMRQQMEESPYQTWPRRGMEPHMSECCEQLEGMDESCRCEGLRMMMRMQQEEMQPRGEQMRRMMRLAENIPSRCNLSPMRCPMGGSIAGF

S0　S1　　　　　　　　　L1　　　　　　　　L2　　　　　　　L3　　　　　　　L4　　　　　　L5　　L6

(SEQ ID NO: 161)

QEECREQMRQQMLS 2-1
CREQMRQQMLSHCR 2-2
QMRQQMLSHCRMYM 2-3
RQQMLSHCRMYMRQQ 2-4
LSHCRMYMRQQMEES 2-5

PRRGMEPHMSECCE 2-6
GMEPHMSECCEQLE 2-7
PHMSECCEQLEGMD 2-8
SECCEQLEGMDESC 2-9
CCEQLEGMDESCRCE 2-10
LEGMDESCRCE 2-11
MDESCRCEGLRMM 2-12
SCRCEGLRMMMR 2-13
SCRCEGLRMMMMRMQQ 2-14
GLRMMMMRMQQEEM 2-15
MMMMRMQQEEMQRP 2-16
MRMQQEEMQPRGEQ 2-17
QQEEMQPRGEQMRR 2-18
EMQPRGEQMRRMMR 2-19
PRGEQMRRMMRLAEN 2-20
EQMRRMMRLAENIPS 2-21
RRMMRLAENIPSRCN 2-22
LAENIPSRCNLSP 2-23
NIPSRCNLSPMRC 2-24
SRCNLSPMRCPMG 2-25
NLSPMRCPMGGS 2-26

FIG. 3B

| FIG. 3B-1 |
| FIG. 3B-2 |

| Epitotes | Sequences | Positions |
|---|---|---|
| S0 | RQQ | 10-12 |
| S1 | CRMYMRQQ (SEQ ID NO:149) | 17-24 |
| L1 | PRRGMEPH (SEQ ID NO: 150) | 34-41 |
| L2 | MDESCRCE (SEQ ID NO: 67) | 52-59 |
| L3 | RMMMMRMQQ (SEQ ID NO: 151) | 62-70 |
| L4 | EMQPRGEQMRRMMR (SEQ ID NO: 152) | 72-85 |
| L5 | NIPSRCN (SEQ ID NO: 153) | 89-95 |
| L6 | PMRC (SEQ ID NO: 154) | 98-101 |

```
    Epitope S1
--------------------
Label   Sequences
--------------------

WT      YMRQQMEE  (SEQ ID NO: 162)
Y20A    AMRQQMEE  (SEQ ID NO: 163)
M21A    YARQQMEE  (SEQ ID NO: 164)
R22A    YMAQQMEE  (SEQ ID NO: 165)
Q23A    YMRAQMEE  (SEQ ID NO: 166)
Q24A    YMRQAMEE  (SEQ ID NO: 167)
M25A    YMRQQAEE  (SEQ ID NO: 168)
```

```
    Epitope L6
--------------------
Label   Sequences
--------------------

WT      NLSPMRC  (SEQ ID NO: 169)
S97A    NLAPMRC  (SEQ ID NO: 170)
P98A    NLSAMRC  (SEQ ID NO: 171)
M99A    NLSPARC  (SEQ ID NO: 172)
R100A   NLSPMAC  (SEQ ID NO: 173)
C101A   NLSPMRA  (SEQ ID NO: 174)
--------------------
```

| 1 | 2 | 3 | 4 | 1 | 2 | 3 | 4 | 5 |
|---|---|---|---|---|---|---|---|---|
| MBNMRP | | | | MBNMRP MC6 | | | | |

←—Fusion construct
←—Target gene only

| 1 | 2 | 1 | 2 | 1 | 2 | 3 | 4 | 1 | 2 | 3 | BNMPR |
|---|---|---|---|---|---|---|---|---|---|---|---|
| MBNMRPMC7 | | MBNMRPMC8 | | MBNMRP MC678 | | | | MBNMRPWBLRP | | | |

0min  30min

0min    5min    15min    30min

EPITOPE IDENTIFICATION AND MODIFICATION FOR REDUCED ALLERGENIC ACTIVITY IN PROTEINS TARGETED FOR TRANSGENIC EXPRESSION

CROSS REFERENCE OF RELATED APPLICATIONS

The present application claims the benefit of U.S. Provisional Application Ser. No. 60/559,732 filed on Apr. 6, 2004, entitled the same, which is explicitly incorporated herein by reference in its entirety.

BACKGROUND OF THE INVENTION

1. Field of the Invention

The present invention is directed to an application of an inventive systematic strategy for mapping, identification and thereby modification of identified allergenic epitope(s) in proteins with significant reduction or total elimination of human IgE-binding activity for transgenic expression.

2. Description of Prior Art

Plants proteins are the primary source of dietary protein for human and livestock. Most plant proteins, however, are nutritionally incomplete, due mainly to their deficient in certain essential amino acids. Recent advances in plant biotechnology offer new approaches to enhance the protein quality (Sun S. S. M. and Larkin B. A., 1992). Altenbach et al. in 1987 first demonstrated that it was feasible to enhance the methionine content by 30% through transferring and expressing of the heterologous Brazil nut methionine-rich protein (BNMRP) gene in tobacco (Conceicao Ada S. et al., 1994). Subsequently, similar approach and methionine enhancement had been confirmed and shown in Arabidopsis (Altenbach S. B. et al., 1989), rapeseed (Altenbach S. B. et al., 1992; Guerche P. et al., 1990), soybean (Townsend I. A. and Thomas L. A., 1994) and other plants (Aragao F. J. et al., 1992; Saalbach I. et al., 1994; Tu H. M. et al., 1998) without negatively affecting agronomic performance.

The BNMRP, abundant and water-soluble in the seed of Brazil nut (Sun S. S. M. et al., 1987), consists of two low molecular weight polypeptide subunit components, an 8.5-kDa polypeptide and a 3.6-kDa polypeptide, associated through disulfide linkages to form a 12-kDa protein molecule (Sun S. S. M. et al., 1987). The mature protein develops from a larger precursor polypeptide of 18 kDa by multiple stepwise proteolytic cleavages post-translationally (Sun S. S. M. et al., 1987) and is targeted to the protein storage vacuoles in seeds through a protein sorting pathway (Saalbach G et al., 1996). This protein contains 18% methionine as revealed by its amino acid and cDNA sequences (Altenbach S. B. et al., 1987; Ampe C. et al., 1986). This finding triggered the idea of using the BNMRP gene to improve the nutritional quality of some important crops such as legumes. It is well known that the seed protein of legumes is nutritionally incomplete, due to its deficiency in methionine, one of the essential amino acids of human and livestock. By traditional plant breeding approach, improvement of the nutritional quality of legume seeds has not been significant (Payne P. I., 1983), presumably due to the lack of methionine-rich protein genes in legume germplasms.

Unfortunately, during the development of this potential improved product, the BNMRP was identified as a major allergen of the Brazil nut, designated Ber e 1, because it could be recognized by most of the sera from patients allergic to Brazil nut (Arshad S. H. et al., 1991; Asero R. et al., 2002; Bartolome B. et al., 1997; Oommen A. et al., 2000; Pastorello E. A. et al., 1998). It was also demonstrated that a protein extract of transgenic soybeans containing the BNMRP had allergenic activities using radioallergosorbent testing, immunoblotting and skin prick testing (Nordlee J. A. et al., 1996). The potential risk of anaphylaxis hampers the use of native BNMRP for protein quality enhancement in transgenic crops, and further efforts in developing and marketing the methionine-enriched transgenic soybean was halted.

The reason why some particular proteins can cause allergic reactions is not well understood. However, it is well-established that the key step to a specific allergic reaction is the binding of at least two IgE antibody molecules to a multivalent allergenic protein. Binding of the allergen-IgE complex to high affinity IgE receptors on most cells and basophils results in activation of most cells and release of mediators responsible for triggering marked allergic inflammatory responses. Thus, identification and characterization of allergen-specific IgE-binding epitopes known to be either linear or conformational appears to be of crucial importance for the molecular approach to reduce or remove the allergenicity of the BNMRP and a better understanding of the allergenic nature of proteins. Most of the IgE epitopes are supposed to be discontinuous, and are very important for the allergenicity of allergens due to the tertiary structure of proteins. However, our knowledge of structural characteristics of conformational IgE binding sites is very limited (Baerga-Ortiz A., 2002; Bredehorst R. and David K., 2001; Bufe A., 2001; Gonzalez E. M. et al., 2002; Karisola P. et al., 2002; Sen M. et al., 2002). In recent years, through the application of synthetic, overlapping peptides representing the entire primary sequence of a given allergenic protein, multiple distinct linear epitopes have been identified for a variety of allergens including those from cow's milk (Busse P. J. et al., 2002; Chatchatee P. et al., 2001; Chatchatee P. et al., 2001; Jarvinen K. M. et al., 2001), soybean (Helm R. M. et al., 2000; Helm R. M. et al., 2000; Xiang P., 2002), shrimp (Ayuso R. et al., 2002; Reese G et al., 1999; Shanti K. N. et al., 1993), peanut (Burks A. W. et al., 1997; Rabjohn P. et al., 1999; Stanley J. S. et al., 1997; Xiang P. et al., 2002), walnut (Robotham J. M. et al., 2002), pollens (Costa M. A. et al., 2000; Hemmens V. J. et al., 1989; Sakaguchi M. et al., 2001; Schramm G. et al., 2001; Soman K. V. et al., 2000; Suphioglu C. et al., 2001) and other sources (Banerjee B. et al., 2000; Beezhold D. H. et al., 2001; Hemmens V. J. et al., 1989; Kahlert H. et al., 1992; Menendez-Arias L. et al., 1990; Mine Y. and Wei Zhang J., 2002; Monsalve R. I. et al., 1993). There are increasing lines of evidence that linear epitopes play a crucial role as IgE binding sites (Bannon G. A. et al., 2001; Beehold D. H. et al., 2001; Helm R. M. et al., 2000). Much effort had been made to identify epitopes on a variety of allergens including those from foods and other sources, and multiple distinct linear IgE recognition sites were elucidated (Ayuso R. et al., 2002; Banerjee B. et al. 2000; Beezhold D. H. et al., 2001; Burks A. W. et al., 1997; Busse P. J. et al., 2002; Chatchatee P. et al., 2001; Chatchatee P. et al., 2001; Costa M. A. et al., 2000; Helm R. M. et al., 2000; Helm R. M. et al., 2000; Hemmens V. J. et al., 1989; Jarvinen K. M. et al., 2001; Kahlert H. et al., 1992; Menendez-Arias L. et al., 1990; Mine Y. and Wei Zhang J., 2002; Monsalve R. I. et al., 1993; Rabjohn P. et al., 1999; Reese G. et al., 1999; Robotham J. M. et al., 2002; Sakaguchi M. et al., 2001; Schramm G et al., 2001; Shanti K. N. et al., Soman K. V et al., 2000; Stanley J. S. et al., 1997; Suphioglu C. et al., 2001; Xiang P. et al., 2002). The major methods in IgE epitope mapping are based on synthetic, overlapping peptides and recombinant peptide libraries (Reese G. et al., 2001), which are subsequently immunoreacted with human IgE to localize the binding sites. For the BNMRP, the 2S albumin from Brazil nut, however, nothing is known about the structural characteristics of both linear and conformational IgE epitopes so far.

SUMMARY OF THE INVENTION

In the invention, the target proteins can be of diverse origins. They may possess biological or pharmaceutical functions and can be applied for human and livestock consumption. Taking advantage of an exceptionally high content (18%) of methionine and an allergenic nature, the Brazil nut methionine-rich protein (BNMRP) was adopted as an example target protein for the production of a sulfur-rich protein with a reduced or negative allergenic activity.

The invention is to provide a systematic method for obtaining a fine IgE epitope mapping of a target protein using the inventive merged strategy of recombinant, overlapping peptides to thereby identify amino acids important for IgE binding within the epitope.

Accordingly, a first aspect of the invention is to provide a modified methionine- and/or cysteine-rich protein having at least one epitope binding to human IgE comprising arginine, in which in the modified protein, the arginine is substituted with alanine or a residue thereof, or with methionine or a residue thereof, so that the modified protein has a reduced or negative allergenic activity.

A second aspect of the invention is to provide a nucleic acid sequence encoding a modified protein defined herein.

According to a third aspect of the invention, there is provided a transgenic plant and/or progeny thereof comprising a modified protein defined herein.

According to a fourth aspect of the invention, there is provided a method for reducing or eliminating human IgE-binding activity of a protein, the protein having at least one epitope binding to human IgE comprising arginine or alanine, the method comprising:
  identifying the epitope of the protein; and
  replacing arginine in the epitope with alanine or a residue thereof, or replacing alanine with methionine or a residue thereof.

According to a sixth aspect of the invention, there is provided a host cell comprising a DNA construct defined herein.

According to a seventh aspect of the invention, there is provided a method for constructing a transgenic plant comprising:
  a) constructing a DNA construct comprising a nucleic acid defined herein operably linked to a vector;
  b) transfecting a plant cell with the construct; and
  c) producing the transgenic plant from the plant cell.

An eighth aspect of the invention is directed to use of a modified protein defined herein in preparing food for animal consumption.

The IgE-binding activity, i.e. the allergenic activity of the modified protein according to the invention and a plant protein produced by the method of the invention can be significantly reduced or eliminated. Therefore, the target protein of the invention can be applied for human and livestock consumption.

Other aspects and features of the invention will be described in detail with reference to the drawings.

BRIEF DESCRIPTION OF THE DRAWINGS

FIG. 1 shows an analysis of IgG and IgE binding with different regions of the 2S methionine-rich allergen (BNMRP) from brazil nut, in which A: Schematic diagram of the fragments of the 12-kDa precursor of the BNMRP as generated by PCR; B: The constructs used to produce the recombinant fusion proteins; C: Expression and immunodetection of the deletion fragments; Lane M, protein markers; Lanes 1-8, samples of polypeptide fragments P1-110, P34-110, P34-85, P60-110, P34-59, P60-85, P86-110 and P1-28 (panel A) respectively; and Lane C, a control.

FIG. 2 shows an epitope mapping of BNMRP using N-terminal deletion method, in which amino acid sequences of the deletions are shown at the left and immunodetection results are shown at the right. Sequence B0, the center region of the large subunit, is designated as SEQ ID NO: 155. Sequences B2-B6 correspond to amino acids 8-26, 10-26, 13-26, 16-26, and 19-26, respectively, of SEQ ID NO: 155. Sequence C0, the center region of the large subunit, is designated as SEQ ID NO: 156. Sequences C1, C2, C3, C4, and C6 correspond to amino acids 4-25, 7-25, 10-25, 13-25, and 19-25, respectively, of SEQ ID NO: 156. Sequence A0, the N-terminal region of the large subunit, is designated as SEQ ID NO: 157. Sequences A1, A2, A3, A5, and A6 correspond to amino acids 4-25, 7-25, 9-25, 15-25, and 18-25, respectively, of SEQ ID NO: 157. Sequence B0, the center region of the large subunit, is designated as SEQ ID NO: 158. Sequences B2-B6 correspond to amino acids 7-26, 10-26, 13-26, 16-26, and 19-26, respectively, of SEQ ID NO: 158. Sequence C0, the C-terminal region of the large subunit, is designated as SEQ ID NO: 159. Sequences C1, C2, C3, C4, and C6 correspond to amino acids 4-24, 7-24, 9-24, 12-24, and 18-24, respectively, of SEQ ID NO: 159. Sequence S0, the small subunit with the internal processed fragment, is designated as SEQ ID NO: 160. Sequences S1-S5 correspond to amino acids 14-34, 17-34, 20-34, 23-34, and 27-34, respectively, of SEQ ID NO: 160.

FIG. 6 shows nucleotide and amino acid sequences of the native and modified BNMRP, in which the specific mutations are highlighted by grayscale background. BNMPR sequence=SEQ ID NO: 175; BNMRP=SEQ ID NO: 176; mBNMRP protein=SEQ ID NO: 177; and mBNMRP=SEQ ID NO: 133.

Figure 7A:
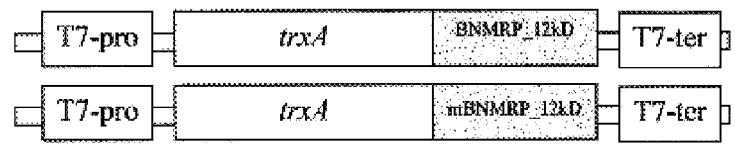
Figure 7B:
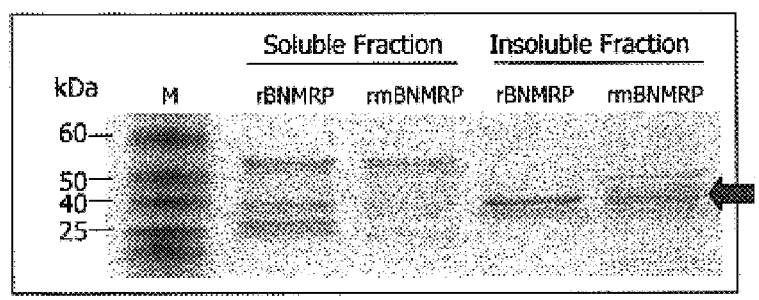

FIG. 7 shows expression of the native and modified BNMRP in *E. coli*, in which Lane M represents protein markers, and rBNMRP and rmBNMRP are the fusion proteins containing the native and modified BNMRP, respectively.

Figure 8:
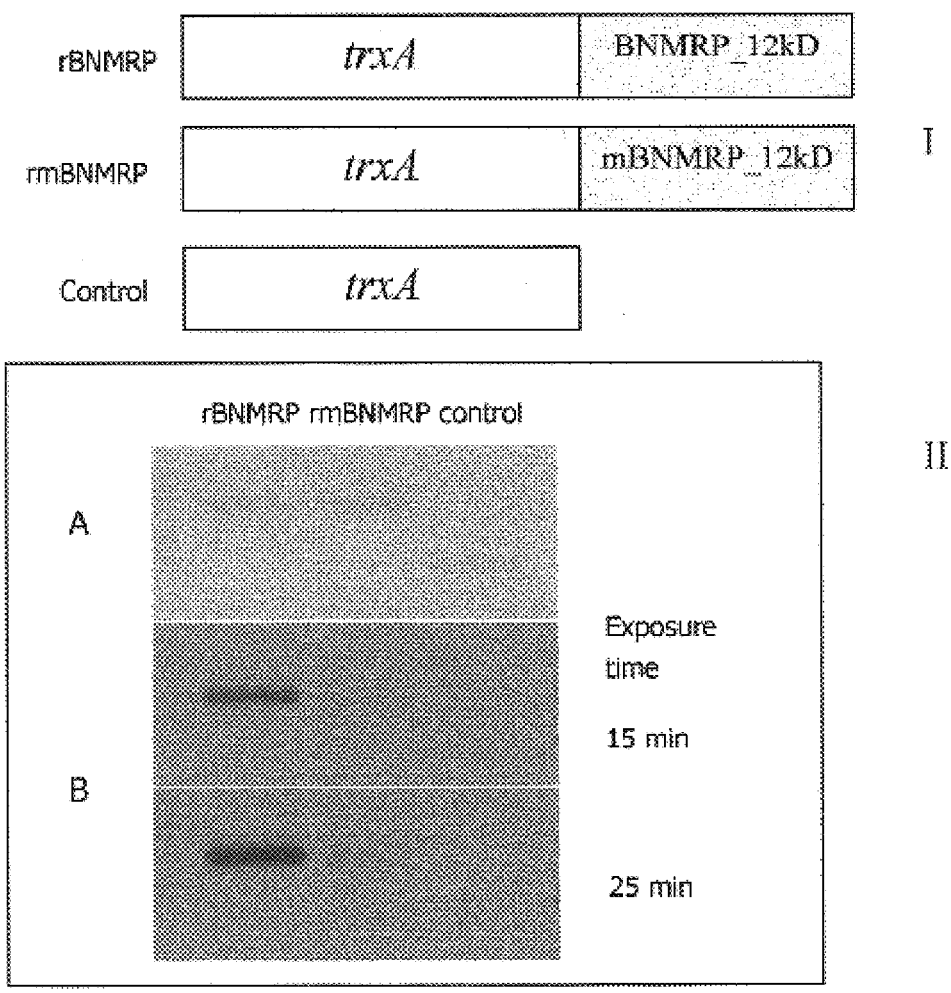

FIG. 8 shows a comparison of IgE binding activity between the native and modified BNMRP, I: Schematic diagram of the fusion proteins, II: Immunodetection of the native (rBNMRP) and modified (rmBNMRP) BNMRP.

Figure 9A:
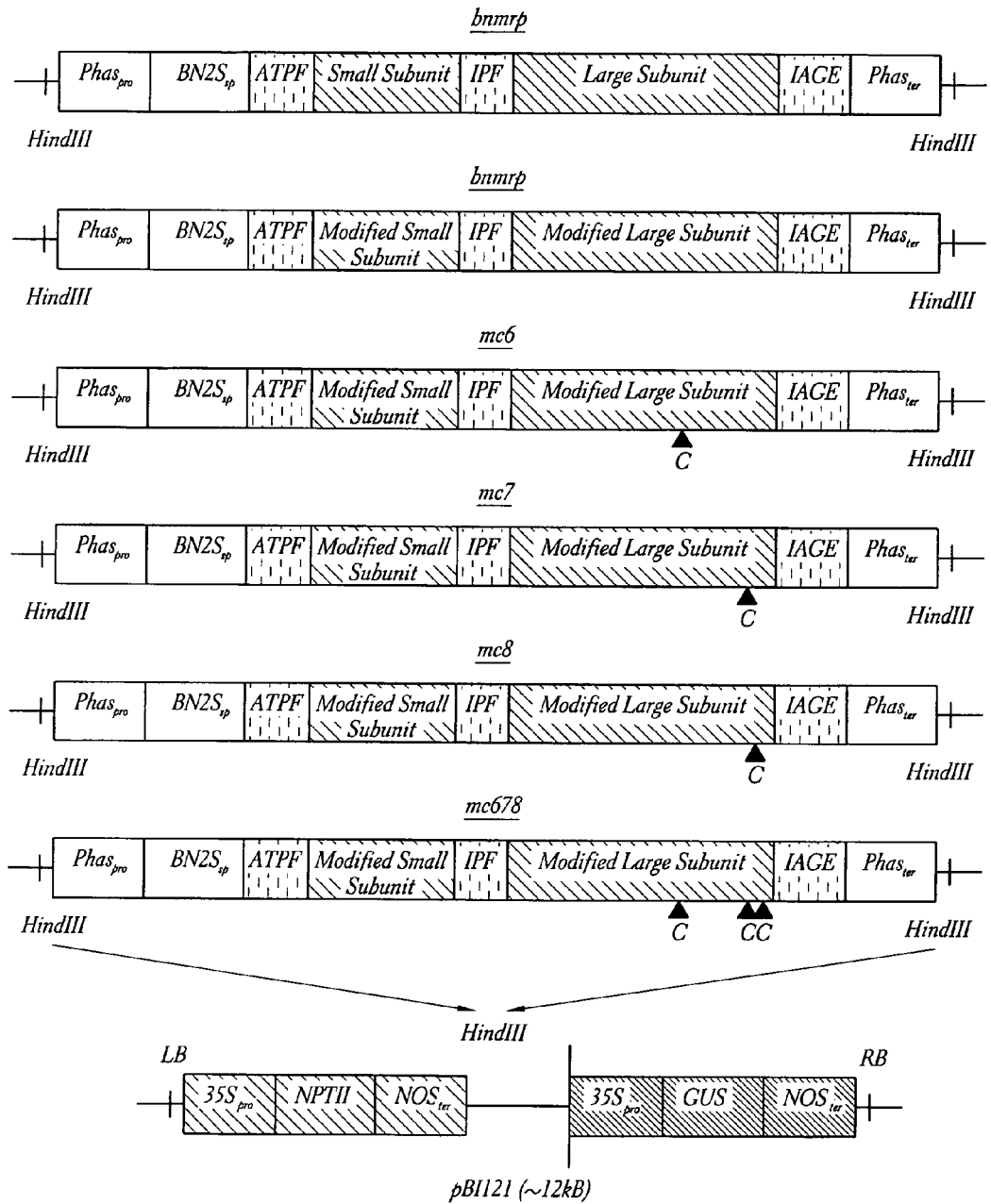
Figures 9, 9A, 9B:
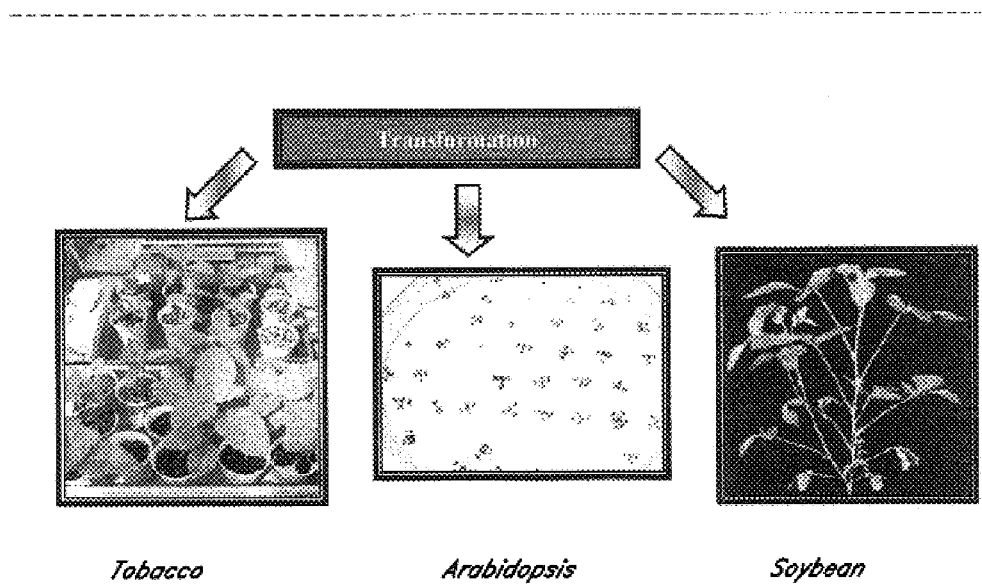

FIG. 9 shows constructs for transforming *Arabidopsis*, tobacco and soybean, bnmrp, coding for native BNMRP; mbnmrp, coding for modified BNMRP; mc6, coding for modified BNMRP with $6^{th}$ cysteine restored; mc7, coding for modified BNMRP with $7^{th}$ cysteine restored; mc8, coding for modified BNMRP with $8^{th}$ cysteine restored; and mc678, coding for modified BNMRP with all cysteine residues restored.

Figure 10:
Figure 10:
Figure 10:
Figure 10:
Figure 10:
Figure 10:
Figure 10:

FIG. 10 summarizes all the constructs transformed into tobacco.

Figure 11A:
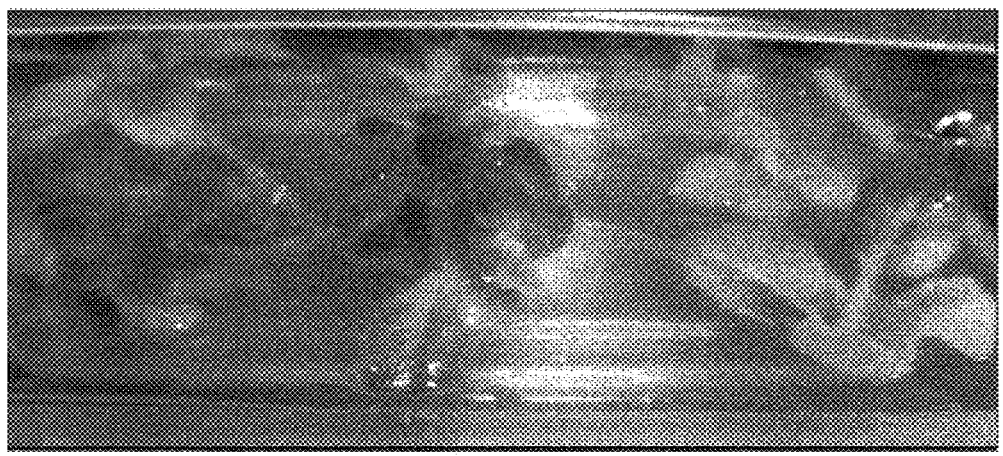
Figure 11B:

FIG. 11 shows the regeneration of tobacco after transformation, in which (a): the regenerated tobacco shoots are placed in rooting medium for root regeneration; and (b) the regenerated plants carrying the target genes were planted in greenhouse for immature and mature seeds.

Figure 12A:
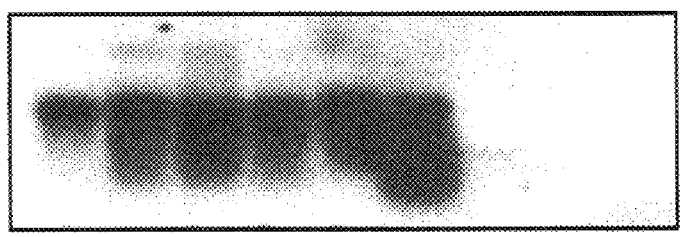
Figure 12B:
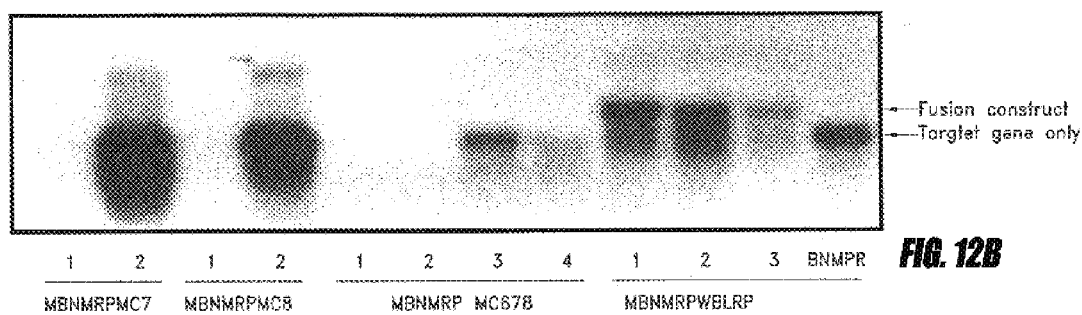

FIG. 12 shows Northern blot of transgenic tobacco plants.

Figure 13A:
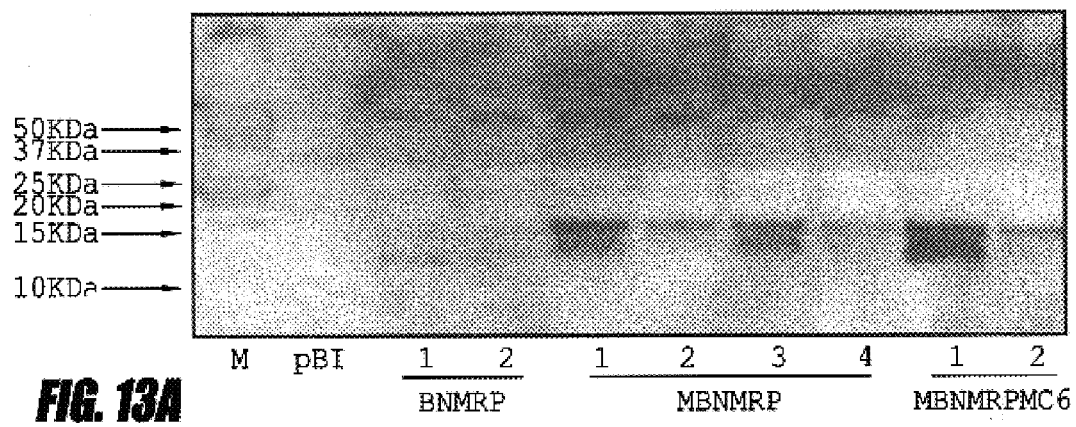
Figure 13B:
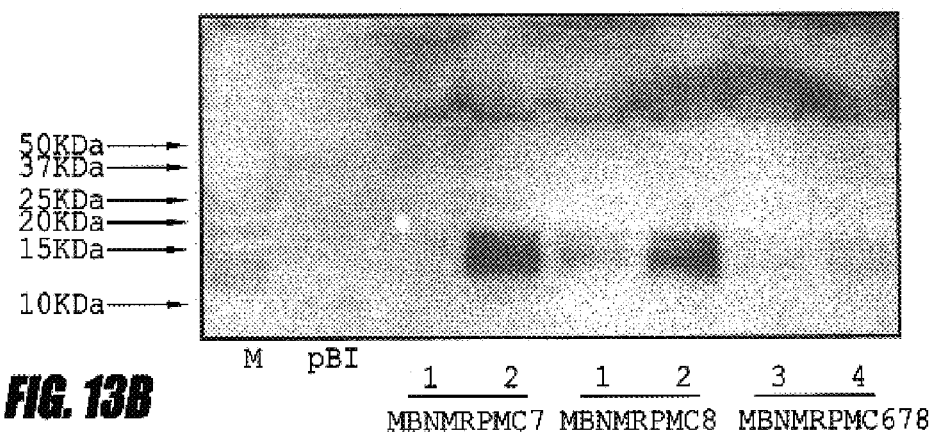
Figure 13C:
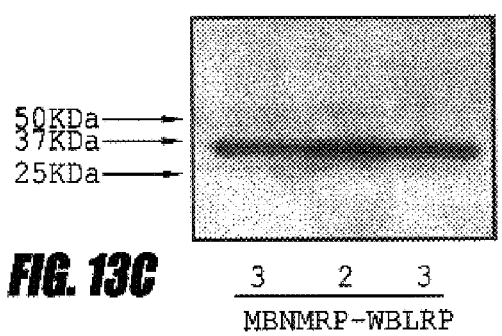

FIG. 13 shows Western detection of MBNMRP and its variants, in which (a) and (b): anti-MBNMRP antibodies ware used to detect the expression of transgenic seeds, and (c): anti-LRP antibodies are used.

Figure 14A:
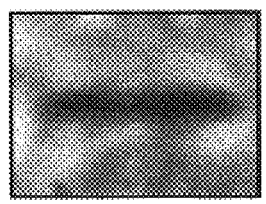
Figure 14B:
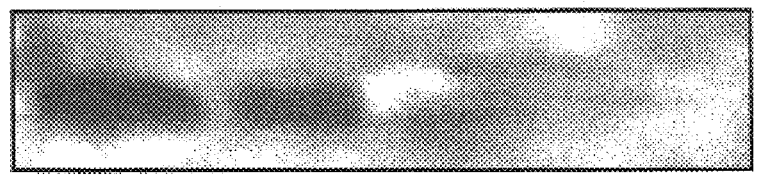

FIG. 14 shows simulated gastric digestion of transgenic proteins, (a): native BNMRP protein from Brazil nut, (b): MBNMRP-WBLRP protein.

DETAILED DESCRIPTION OF THE INVENTION

The present invention provides a modified protein (target protein) and a plant gene expression system which comprises a DNA construct placed operably under the control of a promoter sequence that confers a seed-specific expression. The DNA construct contemplated herein encodes one or more modified proteins and their derivatives which can significantly reduce or negative human IgE-binding activity.

The target protein that can be used in the invention includes those methionine- and/or cysteine-rich proteins, such as a protein of the 2S family of albumin proteins in Brazil nut. Such a modified protein may be used for safer human and livestock consumption and for immunotherapy of brazil-nut allergy by reducing its anaphylactic side effects.

The 2S albumins are storage proteins present in diverse species. Despite high variability in amino acid sequences, the 2S albumins share a similar structure that is heterodimeric and consisting of a large subunit and a small subunit synthesized as a single precursor polypeptide. All the 2S albumins are compact globular proteins with conserved cysteine residues, which are responsible for the disulfur bonds linking the small and the large polypeptides and forming the whole protein. The 2S proteins are abundant in seeds of the plant, providing reserved amino acids during the seed germination and seedling growth.

However, many 2S albumins have been identified as major allergens. The potential to introduce new allergenic proteins into food through plant genetic engineering is of a great concern to public. This issue was first highlighted by our previous study with a 2S methionine-rich protein from Brazil nut (BNMRP). Many other proteins with biological activities, which could have biotechnological applications to improve food quality or to confer improved agronomic performance or resistance to the plant, are also known allergens.

Therefore, carefulness must be taken in choosing safe proteins to use in plant biotechnology, and systems to assess the allergenic potential of foods derived from genetically engineered crop plants have to be in place and enforced to ensure that the potential allergenic proteins are identified before entering the food chain. An attractive alternative is to modify or to design and generate non-allergenic proteins with similar structures and biological properties by genetic engineering for plant improvement.

In this invention, the inventors have adopted the BNMRP as an example for the elucidation and characterization of the IgE epitopes on the target protein and hence, provide significant understanding of the allergenic nature of the 2S allergens. The inventors have successfully demonstrated that it is feasible to modify a protein to be one having a reduced allergenic activity or no longer triggering allergy reactions. This opens up a new approach to enhance the quality of legume proteins without allergenicity, through transferring and expressing the modified methionine-rich and/or cystinerich protein gene(s) for animal feed or human consumption, and restores the public confidence in genetically modified products.

The overall strategy of this invention includes:
1) mapping an epitope of the target protein;
2) identifying amino acids critical to a human IgE binding within the epitope;
3) modifying the epitope and/or related domains to reduce or negative the IgE binding;
4) establishing a plant gene expression system with a recombinant protein from the target protein for the accumulation of the target protein with reduced allergenicity; and
5) confirming the expressed recombinant protein having a reduced or negative allergenic activity.

It is well known that the interaction between an allergen and immune system at the molecular level plays a crucial role in the etiology of allergy. The present invention provides a systematic strategy to identify IgE-binding epitopes on an allergen so that the nature of allergenicity of the allergen can be elucidated.

The inventors have developed a new strategy to identify epitopes on a target proteins by recombinant, overlapping peptides, which merges the advantages of the two existing methods described in the prior art. The recombinant, overlapping peptides, like synthetic, overlapping peptides, ensure a systematic coverage of the entire allergen sequence, whereas it is not possible to ensure the entire allergen sequence is represented in the peptide library. The peptide length of the recombinant, overlapping peptides in the current strategy is not limited to 15 residues as in the case of the SPOTs system, so that it may allow the identification of at least some conformational epitopes. It is also easier to produce and purify the recombinant peptides in large amounts for multiple immunodetections simply by growing and inducing more *E. coli* cells containing the recombinant peptide constructs. Since the recombinant peptides may be fused to trxA at the C-terminus, it is efficient to generate point mutations on the recombinant IgE binding epitopes by PCR, for side-by-side comparison between an unmodified epitope and a mutated epitope. Through this systematic approach, the inventors have identified at least 8 IgE epitopes on one of target proteins, BNMRP, for example, which subsequently allowed the reduction and removal of the IgE binding ability of the methionine-rich allergen by site-directed mutagenesis (described below).

Construction of Recombinant Gene Fragments of Target Proteins

Gene-specific primers for amplifying the target fragments are first designed with restriction enzyme sites for cloning into an expression vector.

Various combinations of primers are applied for amplifying the fragment encoding different gene fragments of the target protein. After sequenced, the PCR products are cloned in an expression vector through the restrictive enzyme sites designed in the primers such as cloned into a pET-30a(+) vector (Novagen) to create different constructs which can express different fusion proteins such as His.tag::BNMRPs::trxA::fliC. A protein without a fragment for target protein is also amplified as a control.

Construction of N-Terminal Deletions of Target Proteins

The clones containing the above cloned fragments are used as templates for producing deletions of the target protein. To generate N-terminal deletions, a series of overlapping primers, offset nine nucleotides encoding 3 amino acids of the target protein are designed. Deletions with a progressive 3-amino acid truncation are generated by PCR with template plasmids. The PCR products are subsequently cloned into a expression vector to form deletion fusion proteins such as His.tag::deletions::trxA::fliC.

Construction of Overlapping, Recombinant Peptides

For generating overlapping, recombinant peptides, each 3' primer is designed with a stop codon to truncate the 3' region of the deletion. The recombinant peptides are constructed by PCR using the combinations of the 3' primers and a promoter primer in the vector (Promega). The amplified fragments are then subcloned into an expression vector, producing small overlapping peptides fused to the C-terminal of a tag.

The recombinant constructs can be expressed in a host cell such as *E. col*. and the recombinant proteins can be purified according to the tags in the fusion proteins. Alternatively, the recombinant proteins can be detected using the method of SDS-PAGE with Coomassie brilliant blue staining or immunoblotting as an example.

Epitope Mapping of Target Proteins

Recombinant proteins containing N-terminal serially deleted proteins, or overlapping peptides of a target protein can be purified and immuno-detected with an anti-polyclonal antibody, or human serum from patients allergic to the target protein. At least 8 linear epitopes have been identified in the BNMRP, one of the preferred embodiments of the invention. An epitope with the strongest IgE reactivity can be consequently mapped.

Figures 3, 3A:
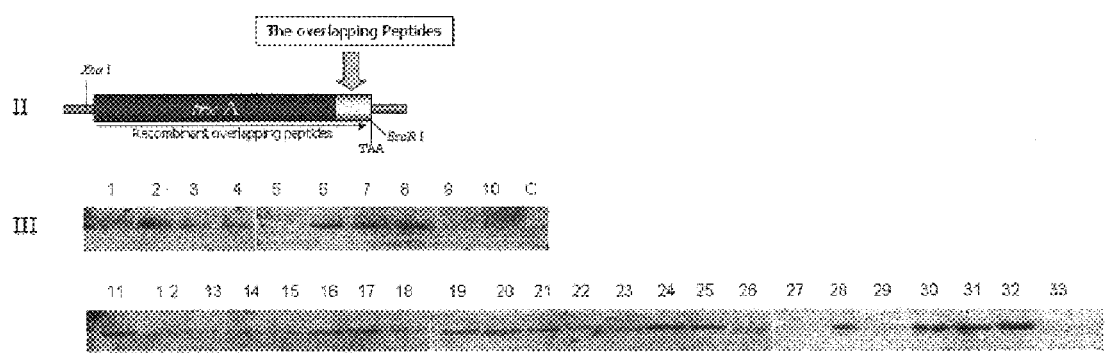
FIG. 3a shows IgE epitope mapping of the BNMRP by using overlapping, recombinant peptides using Set A shorter fragments. The peptide fragments shown in FIG. 3a correspond to the following amino acids (aa) of SEQ ID NO: 161: peptide 1 (aa 1-9); peptide 2 (aa 4-12); peptide 3 (aa 7-15), peptide 4 (aa 10-18); peptide 5 (aa 11-18); peptide 6 (aa 17-24); peptide 8 (aa 20-27); peptide 9 (aa 23-30); peptide 10 (aa26-33); peptide 11 (aa 34-41); peptide 12 (aa 37-44); peptide 13 (aa 40-47); peptide 14 (aa 43-50); peptide 15 (aa 46-53); peptide 16 (aa 49-56); peptide 17 (aa 52-59); peptide 18 (aa 55-64); peptide 19 (aa 60-67); peptide 20 (aa 63-70); peptide 21 (aa 66-73); peptide 22 (aa 69-76); peptide 23 (aa 72-79); peptide 24 (aa 75-82); peptide 25 (aa 78-85); peptide 26 (aa 81-89); peptide 27 (aa 86-92); peptide 28 (aa 89-95); peptide 29 (aa 92-98); peptide 30 (aa 95-101); peptide 31 (aa 98-104); peptide 32 (aa 98-107); and peptide 33 (aa 104-110).

To define the precise position and sequences of epitopes recognized by IgE human serum, the inventors further generates a series of overlapping recombinant peptides covering the entire length of the target protein where IgE binding is observed previously by the deletion approach. In one preferred embodiment, each peptide is 7-8 amino acids in length and progressively offsetting from the previous peptide by 3 amino acids. This approach allows a systematic analysis of the primary sequence of the entire target protein to determine the exact amino acid sequences of the IgE binding regions. For example, as shown in FIG. 3, eight epitopes, designated S0 and S1 on a small subunit and L1-L6 on a large subunit of BNMRP, have been identified in this manner.

Identification of Key Amino Acids Critical to IgE Binding within Identified Epitopes Amino acid substitution analysis of the epitopes shows that mutation of key amino acids to alanine could significantly reduce or eliminate IgE binding. A series of mutants are generated for the identified epitopes by oligonucleotide-mediated mutagenesis using PCR. In each mutant, a selected single amino acid in the native epitope is substituted with an alanine or a residue thereof. If the native amino acid is an alanine, it is replaced by a methionine. This approach allows elucidation of amino acids required in ligand binding within each epitope, since systematic substitution of amino acids with alanine eliminates side chains binding to antibody.

Using the clones containing the native epitopes as templates, PCR is carried out by combination of the vector promoter primer such as a T7 primer and a primer designed to introduce the mutation. Then the PCR products are ligated with a backbone of expression vectors, forming a fusion protein containing the mutated epitope.

The recombinant peptides are probed with an allergic patient's serum to determine the effect of a single amino acid change on the target protein-specific IgE binding. When alanine is substituted for a wild-type amino acid at the position of Arg, the mutated peptide is not recognized by the human serum, or a decrease in binding is observed in the embodiment of the invention. Therefore the mutant position could be identified as a key amino acid critical to IgE binding within the identified epitope.

In the work leading to the present invention, the inventors have demonstrated that arginine or a residue thereof is crucial for IgE binding with the epitope on the target protein such as BNMRP, since all identified epitopes on this molecule contain arginine residues and point mutations of this amino acid within each IgE epitope to alanine result in, without exception, a dramatic decrease or a loss in antibody binding. This positively charged amino acid is the second abundant amino acid (14.85%) in the BNMRP and spreads over the whole protein molecule. The change of the arginine residues by mutation may alter the surface charge as well as the conformational structure of the epitopes or the whole protein molecule, consequently leading to a reduction or a loss in its IgE binding with IgE. This is the first report that a conserved amino acid (Arg) in the epitopes of a food allergen involves in IgE binding.

It is also worth to note that a common structure Arg-Cys, and amino acid sequence Met-Arg harbor IgE binding ability. The sequence similarities suggest the presence of a cross-reacting IgEs capable of recognizing both epitopes on the same protein. This helps to explain the potent nature of the methionine-rich allergen, as in the case of Hev b 5 where in the IgE epitopes 5.7 and 5.8, both having the sequence EKPAE (SEQ ID NO: 178), are cross-reactive (Beezhold D. H. et al., 2001). Although common structural characteristics of linear IgE epitopes are limited so far, the situation may change when more epitope mapping results come in.

Modifications of Epitopes and Related Domains for Reduced Target Protein Specific IgE Binding The present invention encompasses a systematic method for the generation of a derivative of the target protein with a greatly reduced IgE reactivity by point mutation of the identified linear epitopes.

Proteins that can be used in the invention include those rich in methionine and/or cysteine, such as the 2S family of proteins including a protein from Brazil nut, amongst others.

Such a modified protein may be used for a safer human and livestock consumption and for immunotherapy.

Through the application of this systematic approach, the present invention demonstrates that the IgE binding ability of the epitopes can be reduced or removed by mutation of the arginine rather than the methionine in the epitopes, providing the possibility that a modified target protein with reduced IgE binding ability can be generated by mutations without decreasing its methionine content.

Generation of Gene Constructs Encoding Foreign Target Protein with Reduced Allergenicity for Plant Expression The present invention further encompasses a plant gene expression system comprising a DNA construct placed operably under the control of a promoter sequence that confer seed-specific expression. The DNA construct contemplated herein encodes one or more subunits of a sulfur rich-2S seeds storage protein with significantly reduced IgE-binding activity through modifications, more preferably, alanine substitution of the identified epitopes.

The identified epitopes of proteins are modified by site-directed mutagenesis using PCR to generate a specific point mutation for alanine. The PCR products containing the mutations are linked together through the restrictive enzyme site to generate constructs containing a nucleic acid sequence encoding the mutations in epitopes using a similar strategy as described above. Alternatively, some successive overlap extension PCR reactions can be carried out to introduce further specific point mutations in the epitopes. The constructs containing a nucleic acid sequence encoding at least one mutation are introduced into competent host cells for further plant application.

In one embodiment, through the application of the inventive strategy for oligonucleotide-directed mutagenesis, the inventors have generated a recombinant BNMRP clone with mutated epitopes as an example. The inventors chose amino acids in the epitopes that, when changed, resulted in the greatest reduction in IgE binding. Most of the selected amino acids are mutated to alanine. However, in an illustrating engineering, some arginines encoded by the codon AGG in the cDNA are mutated to methionine. Thus, the methionine content of the modified BNMRP is simultaneously increased after mutation.

The relative extent of IgE binding to the altered sequence can be analyzed by SDS-PAGE and probe hybridization with allergic patients' serum against target protein and assessed by densitometry scanning and compared with that of the native one.

The present invention also extends to further engineered variants, including modified proteins with cysteine residues restored, and a lysine-rich protein (e.g. WBLRP) fusion, that are constructed and transformed into target plants for expression such as tobacco for seed-specific expressions.

Different types of plant species, including monocots and dicots, and various transformation techniques can be adopted for the present invention. However, it is preferred to use a plant that can be transformed with high transformation efficiency. Expression vectors containing the target protein expression cassettes can be introduced into plants according to known techniques such as *Agrobacterium*-mediated plant transformation, vacuum infiltration, gene transfer into pollen or calli or protoplast transformation (Bechtold N., et. al., 1993; Fisher D. K. and Guiltinan M. J., 1995). An ordinary skilled person in the art can make use of different strains of bacteria and transformation methods for the transformation of different host plants according to known techniques.

Plant regeneration is well known in the art. Transformants screened for desirable gene products are used for regeneration. The regenerated shoots (leaf-disc technique) or green plants (vacuum infiltration) are transferred in soil and grown in a green house for further expression analysis.

One of the objectives involves the application of a plant seed-specific phaseolin promoter and terminator region to the transgenes, which confines the transgenic expression only in the plant seeds. Another characteristic of this method involves the inclusion of an NPT II and a GUS gene, both driven by a 35S promoter and an NOS terminator. These two genes enable selection of positive transformants during the regeneration of new transgenic plants from calli, and further screening of possible transformants after the regeneration of plant leaves. In one preferred embodiment, all the components are put together into a pBI121 vector, which is an *Agrobacterium tumefaciens*-Ti plasmid system. The inventors has successfully provided in an example a method to make constructs for the transgenic plant seed-specific expression of different variations of MBNMRP. The modified proteins that can be expressed in transgenic plant seeds using this method include the various modified target proteins.

In one example, the inventors have used tobacco (*Nicotiana tabacum*) as the transformation host, since it is well established as a plant model system, and can be easily transformed via *Agrobacterium*-mediated method.

To investigate whether the transgenes integration and expression of recombinant proteins with reduced negative allergenic activity in plants are present in the regenerated tobacco plants, genomic PCR screening, Northern blot analysis for the RNA expressed in the transgenic plants, Western blot analysis for the proteins produced by the engineered variants for example, are performed in the invention. As a result, a plant expressing foreign target protein with reduced allergenicity has been confirmed.

To test if the allergenic activities of these transgenic proteins are hampered, a simulated gastric digestion method is introduced as an example. The inventors have found that MBNMRP in one example showed a significant decrease in thermo-stability than BNMRP, which may reflect a decrease allergenic potential produced by the method of the invention.

The invention is further described with the following examples.

EXAMPLE 1

Construction of N-Terminal Deletions of BNMRP and Overlapping, Recombinant Peptides Construction of Recombinant BNMRP Fragments pHS-3 (Accession Number M17146, ARCO Plant Cell Research Institute, CA, USA), a plasmid containing a cDNA encoding the BNMRP (Altenbach S. B. et al., 1987), was used as a template for PCR cloning of recombinant BNMRP fragments. Gene-specific primers which were shown in Table 1, were designed with restriction enzyme sites for cloning into a pET-30a(+) expression vector (Novagen).

TABLE 1

Primers Used for Fragmentation of BNMRP

| Primers | Sequences (5'-3') | Positions* |
|---|---|---|
| BNLa5 | GCCAGATCTCCCAGGCGGGGAATG (SEQ ID NO:1) | 262-276 |

TABLE 1-continued

Primers Used for Fragmentation of BNMRP

| Primers | Sequences (5'-3') | Positions* |
|---|---|---|
| BNLa3 | CGGACCTCGAGCTTCGCATCTGCAGCT (SEQ ID NO:2) | 325-339 |
| BNLb5 | GCCAGATCTGGCTTAAGGATGATG (SEQ ID NO:3) | 340-354 |
| BNLb3 | CGGACCTCGAGCCCTCATCATCCTTCG (SEQ ID NO:4) | 403-417 |
| BNLc5 | GCCAGATCTCTGGCCGAGAATATC (SEQ ID NO:5) | 418-432 |
| BNLc3 | CGGACCTCGAGCGAACCCGGCAATGGA (SEQ ID NO:6) | 478-492 |
| BNS5 | GCCAGATCACAGGAGGAGTGTCGC (SEQ ID NO:7) | 163-177 |
| BNS3 | CGGACCTCGAGCGCTCTCCTCCATCTG (SEQ ID NO:8) | 232-246 |
| Control 1-5 | CAGACCATGGCTCGAGGTCCGTGC (SEQ ID NO:9) | – |
| Control 1-3 | CCGGGAATTCAAACAGCCCTGCGTTATA (SEQ ID NO:10) | – |

*The position refers to the location of nucleotides in cDNA clone pHS-3 (accession number M17146)

Restriction enzyme site Bgl II was introduced in the 5' primers and Xho I in the 3' primers. Combination of primers BNS5 and BNLc3 was used to amplify the cDNA fragment encoding a 12 kDa precursor (163-492 bp, referring -to the nucleotides of the cDNA clone pHS-3), which contains both a 3-kDa small subunit (163-246 bp) and a 9-kDa large subunit (262-492 bp) linked by the internal processed fragment (247-261 bp). Combination of primers BNS5 and BNS3 was for amplifying the fragment encoding the small subunit of BN2S, and BNLa5 and BNLc3 for the large subunit. The cDNA region coding the large subunit was further fragmented into 3 smaller regions, 262-339 bp, 340-417 bp and 418-492 bp, by PCR using primer combinations BNLa5/BNLa3, BNLb5/BNLb3 and BNLc5/BNLc3, respectively. Two overlapping fragments covering the cDNA of the large subunit, 262-417 bp and 340-492 bp, were also generated using primer combinations BNLa5/BNLb3 and BNLb5/BNLc3, respectively. PCR was performed using a 10 ng DNA template in a 50 µl reaction mixture containing 0.2 µM all the primers, 200 µM dNTPs and 1 unit Taq DNA polymerase (Promega) in 10 mM Tris.HCl, pH8.3, 2 mM $MgCl_2$, 50 mM KCl, 0.1 mg/mL gelatin for 30 cycles: denaturation for 20 sec at 94° C., annealing for 20 secs at 50° C. and extension for 40 sec at 72° C. PCR products were first cloned in a pGEM-T vector (Promega) and confirmed by sequencing on ABI 3100 using a T7 promoter sequencing primer (Promega), then released with Bgl II and Xho I double digestion and cloned into a pFliTrx vector (Invitrogen) between Bgl II and Xho I sites. The BNMRP::trxA::fliC configurations in the resulting recombinant plasmids were released by Bgl II and EcoR I double digestion, and ligated with a BamH I/EcoR I backbone fragment of a pET-30a(+) vector (Novagen) to create 8 constructs, designated as p1-110, p34-110, p34-85, p60-110, p34-59, p60-85, p86-110 and p1-28, forming fusion proteins His.tag::BNMRPs::trxA::fliC.

To produce the control protein, a fragment containing trxA::fliC was amplified from the pFliTrx vector using primers Control 1-5 and Control 1-3 (Table 2), and inserted into the pET-30a(+) vector between the Nco I and EcoR I sites. The resulting construct, named pControl 1, was used to produce the fusion protein His.tag::trxA::fliC as a control protein.

TABLE 2

Primers Used for Construction of N-Terminal Deletions and Overlapping, Recombinant Peptides of BNMRP

| Primers | Sequences (5'-3') | Positions* |
|---|---|---|
| BNa51 | AAGGCCATGGCTGGAATGGAGCCGCACATG (SEQ ID NO:11) | 271-288 |
| BNa52 | AAGGCCATGGCTCCGCACATGAGCGAGTGC (SEQ ID NO:12) | 280-297 |
| BNa53 | AAGGCCATGGCTAGCGAGTGCTGCGAGCAG (SEQ ID NO:13) | 289-306 |
| BNa54 | AAGGCCATGGCTTGCGAGCAGCTGGAGGGG (SEQ ID NO:14) | 298-315 |
| BNa55 | AAGGCCATGGCTCTGGAGGGGATGGACGAG (SEQ ID NO:15) | 307-324 |
| BNa56 | AAGGCCATGGCTATGGACGAGAGCTGCAGA (SEQ ID NO:16) | 316-333 |
| BNa57 | AAGGCCATGGCTAGCTGCAGATGCGAA (SEQ ID NO:17) | 325-339 |
| BNb51 | AAGGCCATGGCTATGATGATGATGAGGATG (SEQ ID NO:18) | 349-366 |
| BNb52 | AAGGCCATGGCTATGAGGATGCAACAGGAG (SEQ ID NO:19) | 358-375 |
| BNb53 | AAGGCCATGGCTCAACAGGAGGAGATGCAA (SEQ ID NO:20) | 367-384 |
| BNb54 | AAGGCCATGGCTGAGATGCAACCCCGAGGG (SEQ ID NO:21) | 376-393 |
| BNb55 | AAGGCCATGGCTCCCCGAGGGGAGCAGATG (SEQ ID NO:22) | 385-402 |
| BNb56 | AAGGCCATGGCTGAGCAGATGCGAAGGATG (SEQ ID NO:23) | 394-411 |
| BNb57 | AAGGCCATGGCTCGAAGGATGATGAGG (SEQ ID NO:24) | 403-417 |
| BNc51 | AAGGCCATGGCTAATATCCCTTCCCGCTGC (SEQ ID NO:25) | 427-444 |
| BNc52 | AAGGCCATGGCTTCCCGCTGCAACCTCAGT (SEQ ID NO:26) | 436-453 |
| BNc53 | AAGGCCATGGCTAACCTCAGTCCCATGAGA (SEQ ID NO:27) | 445-462 |
| BNc54 | AAGGCCATGGCTCCCATGAGATGCCCCATG (SEQ ID NO:28) | 454-471 |
| BNc55 | AAGGCCATGGCTTGCCCCATGGGTGGCTCC (SEQ ID NO:29) | 463-480 |
| BNc56 | AAGGCCATGGCTGGTGGCTCCATTGCCGGG (SEQ ID NO:30) | 472-489 |
| BNs51 | AAGGCCATGGCTCTCAGCCACTGCCGGATG (SEQ ID NO:31) | 202-219 |

TABLE 2-continued

Primers Used for Construction of N-Terminal Deletions and Overlapping, Recombinant Peptides of BNMRP

| Primers | Sequences (5'-3') | Positions* |
|---------|---------|---------|
| BNs52 | AAGGCCATGGCTTGCCGGATGTACATGAGA (SEQ ID NO:32) | 211-228 |
| BNs53 | AAGGCCATGGCTTACATGAGACAGCAGATG (SEQ ID NO:33) | 220-237 |
| BNs54 | AAGGCCATGGCTCAGCAGATGGAGGAGAGC (SEQ ID NO:34) | 229-246 |
| BNs55 | AAGGCCATGGCTGAGGAGAGCCCGTACCAG (SEQ ID NO:35) | 238-255 |
| BNa31 | TTGGAATTCTTATTCGCATCTGCAGCA (SEQ ID NO:36) | 325-339 |
| BNa32 | TTGGAATTCTTAGCAGCTCTCGTCCAT (SEQ ID NO:37) | 316-330 |
| BNa33 | TTGGAATTCTTAGTCCATCCCCTCCAG (SEQ ID NO:38) | 307-321 |
| BNa34 | TTGGAATTCTTACTCCAGCTGCTCGCA (SEQ ID NO:39) | 298-312 |
| BNa35 | TTGGAATTCTTACTCGCAGCACTCGCT (SEQ ID NO:40) | 289-303 |
| BNa36 | TTGGAATTCTTACTCGCTCATGTGCGG (SEQ ID NO:41) | 280-294 |
| BNa37 | TTGGAATTCTTAGTGCGGCTCCATTCC (SEQ ID NO:42) | 271-285 |
| BNb31 | TTGGAATTCTTACCTCATCATCCTTCG (SEQ ID NO:43) | 403-417 |
| BNb32 | TTGGAATTCTTACCTTCGCATCTGCTC (SEQ ID NO:44) | 394-408 |
| BNb33 | TTGGAATTCTTACTGCTCCCCTCGGGG (SEQ ID NO:45) | 385-399 |
| BNb34 | TTGGAATTCTTATCGGGGTTGCATCTC (SEQ ID NO:46) | 376-390 |
| BNb35 | TTGGAATTCTTACATCTCCTCCTGTTG (SEQ ID NO:47) | 367-381 |
| BNb36 | TTGGAATTCTTACTGTTGCATCCTCAT (SEQ ID NO:48) | 258-372 |
| BNb37 | TTGGAATTCTTACCTCATCATCATCAT (SEQ ID NO:49) | 349-363 |
| BNb38 | TTGGAATTCTTACATCATCCTTAAGCC (SEQ ID NO:50) | 340-354 |
| BNc31 | TTGGAATTCTTAGAACCCGGCAATGGA (SEQ ID NO:51) | 478-492 |
| BNc32 | TTGGAATTCTTAAATGGAGCCACCCAT (SEQ ID NO:52) | 469-483 |
| BNc33 | TTGGAATTCTTAACCCATGGGCATCT (SEQ ID NO:53) | 460-474 |
| BNc34 | TTGGAATTCTTAGCATCTCATGGGACT (SEQ ID NO:54) | 451-465 |
| BNc35 | TTGGAATTCTTAGGGACTGAGGTTGCA (SEQ ID NO:55) | 442-456 |
| BNc36 | TTGGAATTCTTAGTTGCAGCGGGAAGG (SEQ ID NO:56) | 433-447 |
| BNc37 | TTGGAATTCTTAGGAAGGGATATTCTC (SEQ ID NO:57) | 424-438 |
| BNc38 | TTGGAATTCTTAATTCTCGGCCAGCCT (SEQ ID NO:58) | 415-429 |
| BNs31 | TTGGAATTCTTACATGGTCTGGTACGG (SEQ ID NO:59) | 247-261 |
| BNs32 | TTGGAATTCTTAGTACGGGCTCTCCTC (SEQ ID NO:60) | 238-252 |
| BNs33 | TTCGAATTCTTACTCCTCCATCTGCTG (SEQ ID NO:61) | 229-243 |
| BNs34 | TTGGAATTCTTACTGCTGTCTCATGTA (SEQ ID NO:62) | 220-234 |
| BNs35 | TTGGAATTCTTACATGTACATCCGGCA (SEQ ID NO:63) | 211-225 |
| BNs36 | TTGGAATTCTTACCGGCAGTGGCTGAG (SEQ ID NO:64) | 202-216 |
| Control 2-3 | TTGGAATTCTTAAGCCATGGC (SEQ ID NO:65) | — |

*The position refers to the location of nucleotides in cDNA clone pHS-3 (accession number M17146)

Construction of N-Terminal Deletions of BNMRP

A clone p1-33, containing the small subunit and the internal processed fragment (FIG. 2, peptide S0), was constructed by the same approach as p1-28 and used as a template for producing deletions of the small subunit, and p 34-59, p 60-85 and p 86-110 as templates for creating deletions of the large subunit. To generate N-terminal deletions, a series of overlapping primers (Table 2, BNa51-BNs55), offset nine nucleotides encoding 3 amino acids of the BNMRP, was designed with a Nco I site at the 5' end. Deletions with a progressive 3-amino acid truncation were generated by PCR with combination of the overlapping primers with the primer Control 1-3 (Table 1) binding to the sites around the EcoR I site of the template plasmids. The PCR products were digested completely or incompletely as needed with Nco I and EcoR I and cloned into the pET-30a(+) vector, forming deletion fusion proteins His.tag::deletions::trxA::fliC.

Construction of Overlapping, Recombinant Peptides

The deletion::trxA::fliC fragments were released from the deletion constructs by Kpn I and EcoR I double digestion and inserted into the pET-32a(+) vector (Novagen) between Kpn I and EcoR I sites, forming the configuration trxA::His.tag::deletions::trxA::fliC, which were used as PCR templates for generating overlapping, recombinant peptides. For each template, a 3' primer (Table 2, BNa31-BNs36), in which a stop codon and an EcoR I site after the stop codon were introduced, was designed to truncate the 3' region of the deletion. The recombinant peptides were constructed by PCR using the combinations of the.3' primers and a T7 promoter primer (Promega). The amplified fragments were digested by Xba I and EcoR I and ligated with the Xba I/EcoR I backbone fragment of the pET-32a(+) vector, producing small overlapping peptides fused to the C-terminal of the trxA::His tag. To generate the control for the recombinant peptides, the original Xba I-EcoR I fragment in pET-32a(+) vector was replaced by a Xba I and EcoR I digested PCR product amplified from pET-32a(+) using the T7 promoter primer and a primer Control 2-3 (Table 2) introducing a stop codon after the restriction enzyme Nco I site of the pET-32a(+) vector, creating pControp1 2, i.e. fusion protein trxA::His.tag.

Expression of Recombinant Peptides in *E. coli*

The recombinant constructs were introduced into *E. coli* strain BL21 (DE3) for expression. Single colonies containing the constructs were selected and grown at 37° C. in 3 mL of an LB medium with appropriate antibiotics. The starting cultures were used to inoculate 100 mL of the LB medium with appropriate antibiotics at 37° C. until $OD_{600}$ reached 0.4-0.6. Cells were induced for 3 hours at 37° C. by addition of IPTG to a final concentration of 1 mM. The induced cells were harvested by centrifugation at 6,000 rpm for 5 min at 4° C. After washing once with 20 mM Tris.HCl, pH8.0, the cells were stored at −70° C. or directly used to purify the induced fusion proteins.

Purification of Recombinant Proteins

The induced fusion proteins were purified using Ni-NTA spin columns (Qiagen) under denaturing conditions. The induced cells were re-suspended in Buffer B (8M urea, 0.1M $NaH_2PO_4$, 0.01M Tris.HCl, pH8.0) and incubated with shaking for 1 hour at room temperature. The supernatants were collected after centrifuging the lysates at 10,000×g for 20 min at room temperature to pellet the cellular debris, and added to the Buffer B pre-equilibrated Ni-NTA spin columns. The columns with the lysate supernatants were centrifuged at 700×g for 2 min, and then washed twice with Buffer C (8M urea, 0.1M $NaH_2PO_4$, 0.01M Tris.HCl, pH6.3). The fusion protein was eluted with 200 μl Buffer E (8M urea, 0.1M $NaH_2PO_4$, 0.01M Tris.HCl, pH4.5). The concentrations of the purified proteins were detected by BCA method.

Tricine-sodium Dedocylsulfate-Polyacrylamide Gel Electrophoresis (SDS-PAGE)

Protein samples were analyzed by Tricine-SDS-PAGE according to Schagger and Jagow (Schagger H. and Jagow G. V., 1987). Proteins were detected by Coomassie brilliant blue staining or immunoblotting.

The experimental process of constructions of recombinant fusion proteins and the results were showed in the FIG. 1, A: schematic diagram of the fragments of the 12-kDa precursor of the BNMRP as generated by PCR; B: the constructs used to produce the recombinant fusion proteins containing the fragments of the BNMRP (1) and the control protein (2). T7-pro, T7 promoter; T7-ter, T7 terminator; BN2Ss, the fragments of the 12-kDa precursor of BNMRP (panel A); trxA, *E. coli* thioredoxin; fliC, *E. coli* flagellin and C: expression and immunodetection of the deletion fragments. The induced *E. coli* lysate was separated on the tricine-SDS PAGE and stained with Coomassie blue (I); the purified proteins stained with Coomassie blue (II); western blot analysis of the purified proteins with BNMRP-specific rabbit polyclonal antiserum (III) and with pooled serum from 9 patients allergic to Brazil nut (IV). Lane M, protein markers; lane 1-8, samples of polypeptide fragments P1-110, P34-110, P34-85, P60-110, P34-59, P60-85, P86-110 and P1-28 (panel A) respectively; and Lane C, a control).

EXAMPLE 2

Epitope Mapping of BNMRP

As shown schematically in FIG. 1, eight overlapping fragments covering the small and large subunits of the BNMRP were generated by PCR. To achieve efficient expression, the fragments were expressed in *E. coli* as fusion proteins with the *E. coli* thioredoxin (trxA) and flagellin (fliC) of a pFlitrx vector. Expression levels were determined by Coomassie brilliant blue staining of proteins after separation by tricine SDS-PAGE. The induced proteins were purified and quantified (FIG. 1*c*). After separation by tricine SDS-PAGE, the fusion proteins were blotted onto nitrocellulose membrane and analyzed for binding with a rabbit anti-BNMRP serum and a pooled human serum from 9 patients allergic to Brazil nut. FIG. 1*c* showed clearly that IgG epitopes were mapped to the middle and C-terminal parts of the large subunit of BNMRP. No IgG reactivity was observed in the small subunit and the N-terminal part of the large subunit. Distribution of IgE epitopes on BNMRP seems more complex than that of the IgG. Except in the control protein, all tested fragments spanning the BNMRP molecule reacted with the pooled human serum. The observation that the small subunit and the three non-overlapping large subunit fragments all reacted with the patients' IgE indicates that each of them harbors at least one linear IgE-binding epitope.

To obtain information on the epitope position and sequence in detail, the inventors established four sets of N-terminus deletions for the small subunit and the three large non-overlapped fragments of the large subunit as shown schematically in FIG. 2. The deletions of the large subunit (A0-A6, B0-B6 and C0-C6) and the small subunit (S0-S5) of BNMRP were generated as fusion proteins in *E. coli*, and purified using Ni-NTA spin columns. 1 μg purified fusion protein per lane was loaded and separated on the tricine SDS-PAGE. After transferring onto nitrocellulose membrane, the deletions of the centre and the C-terminal regions of the large subunit were immunodetected with a BNMRP-specific rabbit polyclonal antiserum to localize the IgG epitope in the BNMRP (A). All deletions of BNMRP were immunodetected with the pooled human serum from 9 patients allergic to Brazil nut (B). Amino acid sequences of the deletions are shown at the left and immunodetection results are shown in the right.

The consecutive deletions were generated by truncating 3 amino acids each time at the N-terminus. For IgG epitope mapping, western blot analysis of the deletions for the middle and C-terminal parts of the large subunit by using the rabbit anti-BNMRP antibody revealed that deletion B6 for the middle fragment of the large subunit and deletions C3, C4, and C5 for the C-terminal part of the large subunit were negative with the antibody, whereas the other deletions for the middle and C-terminal parts of the large subunit were positive with the rabbit antibody. This indicates that for rabbit IgG, there are two epitopes in the large subunit of the BNMRP, one starts with Pro-Arg-Gly in the middle of the large subunit, and the other begins with Ser-Arg-Cys in the C-terminal region of the large subunit.

To map the human IgE epitopes, western blot analysis of the four BNMRP deletion sets was carried out using the pooled patients' serum. For the small subunit, although the inventors failed to generate some of the deletions of the small subunit (FIG. 2), no difference in the extent of the IgE binding signal between the small subunit peptide (S0) and its deletions S1, S2 and S3 was found, indicating that the 13-amino acid region (QEECREQMQRQQM) (SEQ ID NO:66) at the N-terminus of the small subunit at least does not harbor relatively strong epitopes. However, a dramatic reduction in human IgE binding was observed from deletions S1, S2 and S3 to S4 and S5, suggesting that the three amino acids Glu-Met-Arg are very important in the binding of IgE to the small subunit, and this epitope may start with these three amino acids. For the large subunit, all deletions at the N-terminal region showed positive reaction and constant binding signal with the human IgE, suggesting that one IgE epitope is localized on the smallest N-terminal deletion, MDESCRCE (SEQ ID NO:67), of the large subunit. For the centre region of the large subunit, the inventors observed a significant change from relatively strong to weak in the binding of the progressively truncated deletions to IgE when the three amino acids Glu-Met-Gln were removed. This indicates that the position of the epitope on the centre region of the large subunit may begin with the three amino acids Glu-Met-Gln. For the C-terminal region of the large subunit, the inventors found that deletions C1, C2, C3 and C4 gave relatively strong, while the smallest deletion (GGSIAGF) (SEQ ID NO:68) gave reduced IgE binding signal with the pooled patients' sera, indicating that the amino acids (PMRCPM) (SEQ ID NO:69) may be involved in the binding of the C-terminal fragment of the large subunit to IgE and thus an epitope containing these six amino acid can be located in this region. In summary, through immunoblot analysis of the progressively truncated deletions from the N-terminus of the polypeptide, the inventors identify the approximate positions of four epitopes dispersing on the BNMRP molecule.

To define the precise positions and sequences of epitopes recognized by IgE in the pooled human serum, the inventors further generated two series of overlapping recombinant peptides covering the entire length of the small and large subunit. In set A using shorter fragments, each recombinant peptide was 7-8 amino acids in length and progressively offsetting from the previous peptide by 3 amino acids while in set B the peptide length was longer, comprising 13-16 amino acids. The results from these two sets of fragments are complementary to each other as set A peptides defines the position of these epitopes in a higher solution while the set B peptides aids in identifying longer epitopes which might be fragmented in set A peptides. All peptides were produced as trxA fusion protein in the E. coli expression system, as depicted in FIG. 3. This approach allows systematic analysis of the entire BNMRP primary sequence to determine the exact amino acid sequences of the IgE binding regions.

The overlapping, recombinant peptides method and the results were showed in FIG. 3a, A: the sequences of the 12-kDa precursor of the BNMRP and the overlapping peptides; B: the constructs for expressing overlapping, recombinant peptides and C: Western blot analysis of the purified overlapping peptides (a) with a pool of sera from 9 patients allergic to Brazil nut (b).

As shown in FIG. 3a, eight epitopes, designated S0 and S1 on the small subunit and L1-L6 on the large subunit, were identified in set A peptides. For the small subunit, a significant IgE reactivity was observed with the epitope S1 encompassing three peptides #6, 7 and 8, wherein amino acids Tyr-Met overlapped. Among the other six epitopes spreading along the large subunit molecule, the strongest IgE reactivity was shown by epitope L4 locating within peptides #24, 25 and 26 as well as L6, locating within peptides #30, 31 and 32. It is likely that Pro-Arg-Gly-Glu-Gln-Arg-Arg-Met-Met-Arg (SEQ ID NO:70) is essential for IgE binding to epitope L4, while Pro-Met-Arg-Cys (SEQ ID NO:71) is essential for IgE binding to epitope L6. The observation that two epitopes, L3 and L4, were separately localized in the two methionine-rich regions of the large subunit caused concerns, in consideration of their subsequent necessity of amino acid modification.

Figure 3B:
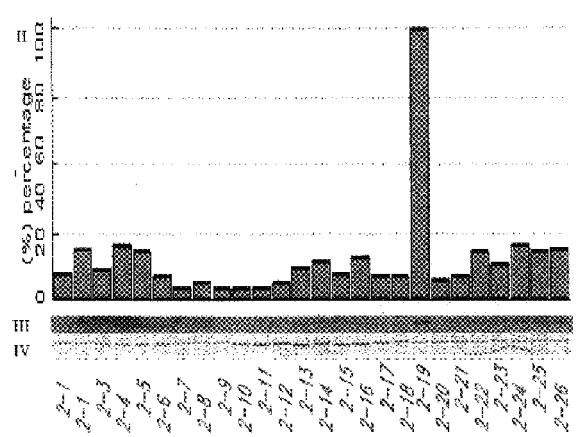
FIG. 3b shows determination of the length of the longest and strongest epitope (L4) in BNMRP using Set B longer fragments. The peptide fragments shown in FIG. 3b correspond to the following amino acids (aa) of SEQ ID NO: 161: peptide 1 (aa 1-15); peptide 2 (aa 4-18); peptide 3 (aa 7-21); peptide 4 (aa 10-24); peptide 5 (aa 14-28); peptide 6 (aa 34-47); peptide 8 (aa 40-53); peptide 9 (aa 43-56); peptide 10 (aa 45-59); peptide 11 (aa 49-59); peptide 12 (aa 52-64); peptide 13 (aa 55-67); peptide 14 (aa 55-70); peptide 15 (aa 60-73); peptide 16 (aa 63-76); peptide 17 (aa 66-79); peptide 18 (aa 69-82); peptide 19 (aa 72-85); peptide 20 (aa 75-89); peptide 21 (aa 78-92); peptide 22 (aa 81-95); peptide 23 (aa 86-98); peptide 24 (aa 89-101); peptide 25 (aa 92-104); and peptide 26 (aa 95-106).

As showed in the FIG. 3b, twenty six overlapping, recombinant 13 to 16-amino acid peptides, offset by 3-amino acids, were generated by a PCR strategy. The amino acid sequence of the 12-kDa precursor of BNMRP was shown at the top, and the amino acid sequences of the overlapping, recombinant peptides were shown under that of the 12-kDa precursor in Panel I. Peptides 2-1 to 2-5 cover the entire length of the small subunit, while peptides 2-6 to 2-26 cover the large subunit. The peptides were produced in E. coli. (IV) and immunodetcted (III) as in FIG. 3a. Lanes 2-1 to 2-26 were samples of the overlapping, recombinant peptides #2-1 to 2-26, as shown in panel I, respectively. IgE binding reactivity of the recombinant peptides was determined by densitometry and shown in Panel II.

The inventors then fine tuned the epitope mapping by using set B peptides (FIG. 3b). This fine tuning, while confirming the findings of set A peptides, led to higher binding activity of the recombinant peptides encompassing the eight identified epitopes to IgE. And epitope L4 (Glu-Met-Gln-Pro-Arg-Gly-Glu-Gln-Arg-Arg-Met-Met-Arg) (SEQ ID NO:72), the longest epitope with the strongest binding activity to the pooled human antisera (FIG. 3b-II), was identified in this refinement.

Figure 4:
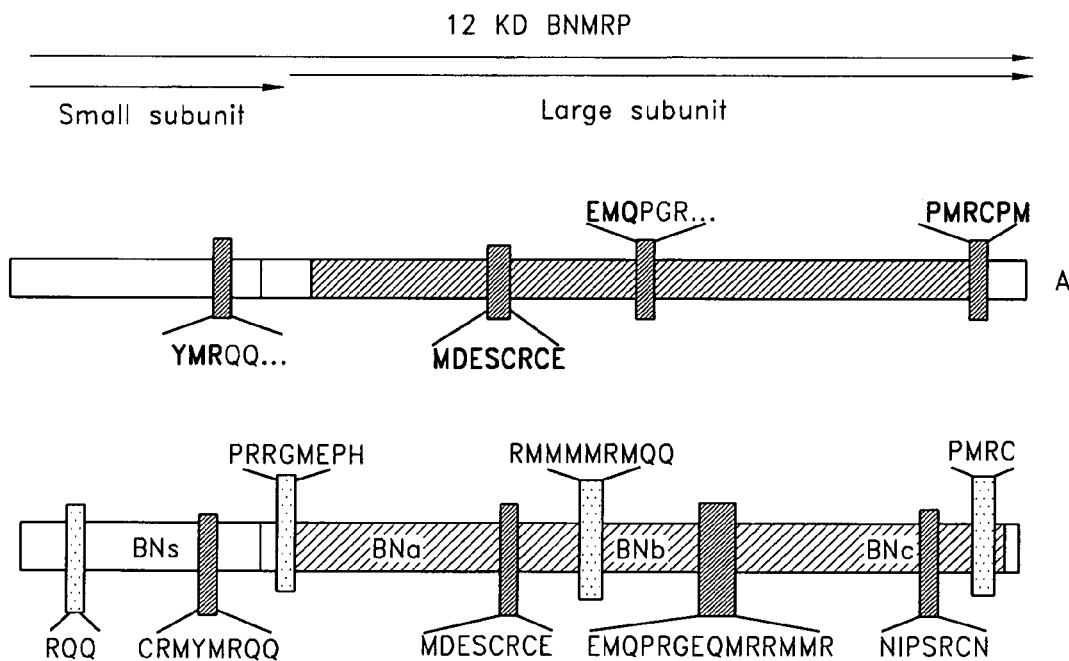
FIG. 4 shows comparison of the epitopes identified by deletion and overlapping peptide approaches.

The epitope positions obtained by both deletion mapping and overlapping recombinant peptide strategies were compared in FIG. 4. The positions of all four epitopes identified by deletion analysis are in accordance with that identified by overlapping peptide strategy. FIG. 4 also summarizes the epitopes identified on the BNMRP molecule. It is worth to note that all regions containing amino acid sequences Arg-Cys or Met-Arg on the BNMRP molecule harbor the IgE binding ability.

At least 8 linear epitopes were thus identified in the BNMRP (FIGS. 2-4). The epitope with the strongest IgE reactivity was mapped to the C-terminal region of the large subunit. The methionine-rich regions in the large subunit were also found to harbor IgE-binding ability.

EXAMPLE 3

Identification of Key Amino Acids Critical to IgE Binding within Identified Epitopes Modification of Epitopes by Alanine Substitution Using the clones containing the native epitopes as templates, PCR was carried out using pfu DNA polymerase by combination of the T7 promoter primer and a primer designed to introduce the mutation, as shown in Table 3. After digestion with Xba I, the PCR product was ligated with the Xba I/EcoR V backbone of the pET-32a(+) vector, forming the fusion protein containing the mutated epitope fused to the C-terminal of the trxA::His.tag.

The strong epitopes L6 and S1 and the two methionine-rich regions associated epitopes L3 and L4 were chosen to identify amino acids that are important for IgE binding in each of the epitopes. The native and mutated peptides were produced in E. coli as trxA fusion proteins. Expression was quantified by Coomassie brilliant blue staining of proteins after separation by tricine SDS-PAGE. The recombinant peptides were probed with the pooled Brazil-nut allergic patients' serum to determine the effect of single amino acid change on Brazil nut-specific IgE binding.

TABLE 3

Primers Used for Alanine Substitution Analysis of BNMRP Epitopes

| Primers | Sequences (5'-3') | Resulting Mutants |
|---|---|---|
| MES1-1 | CTTACATGTACATCCGGCATGCGCTGAG (SEQ ID NO:73) | H16A |
| MES1-2 | CTTACATGTACATCCGTGCGTGGCTGAG (SEQ ID NO:74) | C17A |
| MES1-3 | CTTACATGTACATTGCGCATTGGCTGA (SEQ ID NO:75) | R18A |
| MES1-4 | CTTACATGTAAGCCCGGCATTGGCT (SEQ ID NO:76) | M19A |
| MES1-5 | CTTACATTGCCATCCGGCATTG (SEQ ID NO:77) | Y20A |
| MES1-6 | CTTATGCGTACATCCGGCATTG (SEQ ID NO:78) | M21A |
| MES2-1 | CTTACTCCTCCATCTGCTGTCTCATTGCAGCCAT (SEQ ID NO:79) | Y20A |
| MES2-2 | CTTACTCCTCCATCTGCTGTCTTGCGTAAGC (SEQ ID NO:80) | M21A |
| MES2-3 | CTTACTCCTCCATCTGCTGCCATGTA (SEQ ID NO:81) | R22A |
| MES2-4 | CTTACTCCTCCATCTGCTCTCATGTA (SEQ ID NO:82) | Q23A |
| MES2-5 | CTTACTCCTCCATCGCCTGTCTCAT (SEQ ID NO:83) | Q24A |
| MES2-6 | CTTACTCCTCAGCCTGTCTCAT (SEQ ID NO:84) | M25A |
| MEL3-1 | CTTACCTCATCATCATCATCGCTAAGCC (SEQ ID NO:85) | R62A |
| MEL3-2 | CTTACCTCATCATCATCGCCCTTAAGCC (SEQ ID NO:86) | M63A |
| MEL3-3 | CTTACCTCATCATCGCCATCCTTAAGCC (SEQ ID NO:87) | M64A |
| MEL3-4 | CTTACCTCATCGCCATCATCCTTAA (SEQ ID NO:88) | M65A |
| MEL3-5 | CTTACCTCGCCATCATCATCCT (SEQ ID NO:89) | M66A |
| MEL3-6 | CTTACGCCATCATCATCATCCT (SEQ ID NO:90) | R67A |
| MEL4-1 | CTTACTGTTGCATCCTCATCGCCATCAT (SEQ ID NO:91) | M65A |
| MEL4-2 | CTTACTGTTGCATCCTCGCCATCATCAT (SEQ ID NO:92) | M66A |
| MEL4-3 | CTTACTGTTGCATCGCCATCATCATCAT (SEQ ID NO:93) | R67A |
| MEL4-4 | CTTACTGTTGCGCCCTCATCATCA (SEQ ID NO:94) | M68A |
| MEL4-5 | CTTACTGTGCCATCCTCATCA (SEQ ID NO:95) | Q69A |
| MEL5-1 | CTTACCTTCGCATCTGCGCCCCTCG (SEQ ID NO:96) | E78A |
| MEL5-2 | CTTACCTTCGCATCGCCTCCCCTCG (SEQ ID NO:97) | Q79A |
| MEL5-3 | CTTACCTTCGCGCCTGCTCCCCTCG (SEQ ID NO:98) | M80A |
| MEL5-4 | CTTACCTTGCCATCTGCTCCCCTCG (SEQ ID NO:99) | R81A |
| MEL5-5 | CTTACGCTCGCATCTGCTCCCC (SEQ ID NO:100) | R82A |
| MEL6-1 | CTTACTCGGCCAGCCTCATCATCGCTCGAGC (SEQ ID NO:101) | R82A |
| MEL6-2 | CTTACTCGGCCAGCCTCATCGCCCTTCG (SEQ ID NO:102) | M83A |
| MEL6-3 | CTTACTCGGCCAGCCTCGCCATCCTTCG (SEQ ID NO:103) | M84A |
| MEL6-4 | CTTACTCGGCCAGCGCCATCATCCTTCG (SEQ ID NO:104) | R85A |
| MEL6-5 | CTTACTCGGCCGCCCTCATCATCCTTCG (SEQ ID NO:105) | L86A |
| MEL6-6 | CTTACTCCATCAGCCTCATCATCCTTCG (SEQ ID NO:106) | A87M |
| MEL8-1 | CTTAGCATCTCATGGGAGCGAGGTT (SEQ ID NO:107) | S97A |
| MEL8-2 | CTTAGCATCTCATGGGCACTGAGGTT (SEQ ID NO:108) | P98A |
| MEL8-3 | CTTAGCATCTAGCGGGACTGAGGTT (SEQ ID NO:109) | M99A |
| MEL8-4 | CTTAGCATGCCATGGGACTGAGGTT (SEQ ID NO:110) | R100A |
| MEL8-5 | CTTAGGCTCTCATGGGACTGAGGTT (SEQ ID NO:111) | C101A |

Figure 5:
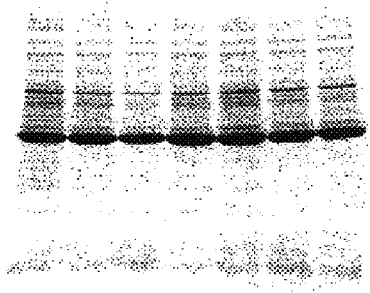
FIG. 5 shows that IgE binding ability of the epitopes of BNMRP can be reduced or removed by mutation, the native and mutated peptides are produced as fusion proteins in *E.* coli and separated on tricine SDS-PAGE and visulized by Coomassie blue staining (A), or immunodetection with the pooled human serum of Brazil nut allergic patients (B).
Figure 5:
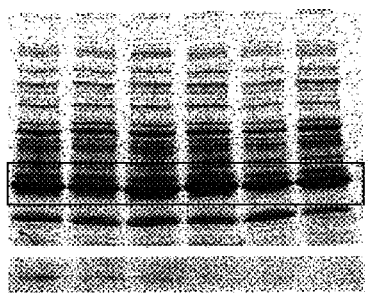

FIG. 5 showed the results of immunoblot strips containing the wild-type and mutant peptides for epitopes L6 and S1. When alanine was substituted for the wild-type amino acid at positions $Arg^{20}$, Arg22, Arg100 and Cys101, the mutated peptides were not recognized by the pooled human serum, or a decrease in binding was observed. It is interesting to note that an alanine substitution increased IgE binding at positions Gln24. The remaining epitopes were analyzed in the same manner. In general, the IgE binding ability of each epitope could be largely reduced by replacing the wild-type amino acid residue with alanine. The essential residues for IgE binding within each tested epitope were shown in Table 4. In fact, a reduction or loss in IgE binding was observed without exception in all the mutants when an alanine substitution was made at a position where the native residue is arginine. An alanine substitution of the sequence motif Met-Arg and Arg-Cys also led to a decrease or loss of IgE binding.

FIG. 4 showed the comparison of the epitopes identified by deletion and overlapping peptide approaches. The 12-kDa precursor of BNMRP is schematically represented by transverse bar. The small (BNs) and the large (BNa,b,c) subunits of the BNMRP are marked with white and grayscale boxes respectively; both the internal and the C-terminal processed fragments are marked with black box. The epitopes identified by deletion (YMRQQ (SEQ ID NO:122). . . . , MDESCRCE (SEQ ID NO:67), EMQPRG (SEQ ID NO:113). . . . , PMRCPM (SEQ ID NO:69)) (A) and that by combined results of overlapping peptide set A and B (S0-S1, L1-6) (B) strategies are represented by vertical bars with their sequences.

It was also worth to note that three of the epitopes on the large subunit, L2, L5 and L6 in the target protein of BNMRP, contain a common structure Arg-Cys, and all regions around the amino acid sequence Met-Arg in the BNMRP molecule harbor IgE binding ability. The sequence similarities suggest the presence of a cross-reacting IgEs capable of recognizing both epitopes on the same protein, making BNMRP a multi-valent allergen, as in the case of Hev b 5 where in the IgE epitopes 5.7 and 5.8, both having the sequence EKPAE (SEQ ID NO: 178), are cross-reactive (Beezhold D. H. et al., 2001).

TABLE 4

Amino Acids in Epitopes Required for IgE Binding

| Epitopes | Amino Acid Sequences | Positions |
| --- | --- | --- |
| S1 | LSHCRMYMRQQMEE (SEQ ID NO:114) | 14-27 |
| L3 | GLRMMMMRMQQ (SEQ ID NO:115) | 60-70 |
| L4 | EMQPRGEQMRRMMRLAE (SEQ ID NO:116) | 72-88 |
| L6 | NLSPMRC (SEQ ID NO:117) | 95-101 |

The BNMRP IgE epitopes are presented by single-letter amino acid code. The position of each peptide refers to the location of amino acids in the 12 kDa precursor of the BNMRP. The tested amino acids were indicated by bold letters. The amino acids, when altered, led to a decrease in IgE binding are underlined.

EXAMPLE 4

Modifications of Epitopes and Related Domains for Reduced Target Protein Specific IgE Binding The identified epitopes of target proteins were modified by site-directed mutagenesis using PCR to generate specific point mutation for alanine. Primers used to mutate the cDNA of the BNMRP were adopted as listed in Table 5. First, the clone pHS-3 was used as a template for 6 separate PCR reactions. Reaction 1 used a primer pair MBN1 and BNF3, reaction 2, MBN2 and BNF3; reaction 3, MBN3 and BNF5; reaction 4, BNF5 and MBN4; reaction 5, BNF3 and MBN6 and reaction 6, BNF5 and MBN7. The PCR products in the reaction mixtures were separated from the template (pHS-3) by agarose gel electrophoresis and recovered. The purified PCR products of reactions 1, 2 and 3 were cloned into a pGEM-T vector to create pGEM-mS1, pGEM-mL3 and pGEM-mL2, which contain the specific point mutations in epitopes S1, L3 and L2 of the BNMRP, respectively. The PCR product of reaction 4 was used as a template for another PCR reaction using primers BNF5 and MBN5, of which the 15 nucleotides at the 3' end overlaps with those at 5' end of a primer MBN4. The resulting PCR product was cloned into a pGEM-T vector to create pGEM-mL5L6. The two PCR products of reactions 5 and 6 were combined and used as templates for an overlap extension PCR reaction (Ho S. N. et al., 1989), using primers BNF3 and BNF5. The PCR product was cloned into the pGEM-T vector to create pGEM-mS1. The DNA fragments containing the point mutations in pGEM-mS0 and pGEM-mS1 were released by double digestions of AlwN I+Sac II, and AlwN I+Apa I, respectively, and combined and ligated with a pBluescript SK(+) vector cleaved by Apa I and Sac II, producing pBS-mS0S1. The inserts in pGEM-mL2 and pGEM-mL3 were first excised by Ase I+Not I and Ase I+EcoR I digestions, respectively, then combined and ligated with the EcoR I/Not I backbone fragment of the pBluescript SK(+) vector to create a pBS-mL2L3. The Ase I site was introduced between the epitopes L2 and L3 through the primers MBN2 and MBN3, by changing the codon usage of the glycine 96 of the 18-kDa BNMRP precursor to facilitate the combination of the mutated IgE epitopes L2 and L3. The insert in pGEM-mL5L6 was released by Nco I and Sac II and ligated with the Nco I/Sac II backbone fragment of pBS-mL2L3 to produce pBS-mL5L6. In this construct, a short DNA fragment after the Nco I site at the 3' end of the BNMRP coding region from pBS-mL2L3 was added to the 3' end of the insert from pGEM-mL5L6 to complement the open reading frame of the mutated BNMRP cDNA. The DNA fragments containing the mutations in pBS-mS0S1 and pBS-mL2L3 were linked together through the Pvu II site to generate pBS-mS0S1L2L3 using a similar strategy as above. The mutations in pBS-mL5L6 were integrated into pBS-mS0S1L2L3 through Ava I site, resulting in pBS-mS0S1L2L3L5L6. Subsequently, two successive overlap extension PCR reactions were carried out, using two complementary primers pairs MBN8/MBN9 and MBN10/MBN11, to introduce specific point mutations in epitopes L1 and L4 of mS0S1L2L3L5L6, resulting in a final BNMRP mutant (mBNMRP). The mBNMRP was cloned into a pGEM-T vector to create a pGEM-mBNMRP. The cDNA fragment encoding the 12kDa-precursor of the mBNMRP was amplified from pGEM-mBNMRP using the following primers: 5'-CATGC-CATGGCTCAGGAGGAGTGTGCC-3' (SEQ ID NO:118) and 5'-TGGGAATTCTTAGAACCCGGCAATGGA-3' (SEQ ID NO:119). After digestion by EcoR I and incomplete digestion by Nco I, the cDNA fragment was ligated with Nco I/EcoR I backbone fragment of pET-32a(+) to create a pET-mBNMRP 12. Another construct, designated pET-BNMRP 12, was produced as a positive control of pET-mBNMRP12 using a cDNA fragment coding the 12-kDa precursor of the BNMRP instead of that of the mBNMRP in pET-mBNMRP 12. pControl 2 was served as negative control. The constructs were introduced into the competent BL21trxB (DE3) pLysS cells for further plant application.

TABLE 5

Primers Used for Site-Directed Mutagenesis of BNMRP

| Primers | Sequences (5'-3') | Positions* |
| --- | --- | --- |
| BNF5 | TGGGTCTACATGGCGAAGATTTCA (SEQ ID NO:120) | 55-69 |
| BNF3 | TGGGTATACTCAGAACCCGGCAAT (SEQ ID NO:121) | 481-495 |
| MBN1 | CTCAGCCACTGCGCGATGGCCATGGCACAGCAG (SEQ ID NO:122) | 202-234 |
| MBN2 | GGATTAATGATGATGATGATGATGGCACAG GAG (SEQ ID NO:123) | 340-375 |
| MBN3 | CATTAATCCTTCGGCTGCGCAGCTCTC (SEQ ID NO:124) | 322-348 |

TABLE 5-continued

Primers Used for
Site-Directed Mutagenesis of BNMRP

| Primers | Sequences (5'-3') | Positions* |
|---|---|---|
| MBN4 | CATAGGACTGAGGTTGGCGGCGGAAGGGAT (SEQ ID NO:125) | 430-459 |
| MBN5 | ACCCATGGGGGCTGCCATAGGACTGAGGTT (SEQ ID NO:126) | 445-474 |
| MBN6 | GAGTGTGCCGAGCAGATGCAGGCACAGCAGATG (SEQ ID NO:127) | 169-201 |
| MBN7 | CTGCTGTGCCTGCATCTGCTCGGCACACTCCTC (SEQ ID NO:128) | 169-201 |
| MBN8 | ACCATGCCCGCGGCGGGAATGGAG (SEQ ID NO:129) | 256-279 |
| MBN9 | CTCCATTCCCGCCGCGGGCATGGT (SEQ ID NO:130) | 256-279 |

```
atggcgaaga tttcagttgc ggcagcagcc ctccttgtcc tcatggccct cggccacgcc    60   (SEQ ID NO:133)
accgccttcc gggccaccgt caccaccaca gtggtggagg aggagaacca ggaggagtgt   120
gccgagcaga tgcaggcaca gcagatgctc agccactgcg cgatggccat ggcacagcag   180
atggaggaga gcccgtacca gaccatgccc gcggcgggaa tggagccgca catgagcgag   240
tgctgcgagc agctggaggg gatggacgag agctgcgcag ccgaaggatt aatgatgatg   300
atgatgatga tggcacagga ggagatgcaa ccccgagggg agcagatgcc attgatgatg   360
atgctggccg agaatatccc ttccgccgcc aacctcagtc ctatggcagc ccccatgggt   420
ggctccattg ccgggttctg a.                                             441
```

TABLE 5-continued

Primers Used for
Site-Directed Mutagenesis of BNMRP

| Primers | Sequences (5'-3') | Positions* |
|---|---|---|
| MBN10 | GAGCAGATGGCAATGATGATGATGCTGGCCGAG (SEQ ID NO:131) | 394-426 |
| MBN11 | CTCGGCCAGCATCATCATCATTGCCATCTGCTC (SEQ ID NO:132) | 394-426 |

*The position of the primer binding sites refers to the location of nucleotides in cDNA clone pHS-3 (accession number M17146)

FIG. 5 showed that the IgE binding ability of the epitopes of BNMRP could be reduced or removed by mutation. Epitopes S1 and L6 were generated with an alanine residue substituted for one of the amino acids at each position in the peptides by a PCR based approach. The amino acid sequences of the native (WT) and the mutated (Y20A, M21A, R22A, Q23A, Q24A and M25A for epitope S1 and S97A, P98A, R100A and C101A for epitope L6) peptides were shown at the left, and the mutated residues in the peptides are marked by bold. The native and mutated peptides were produced as fusion proteins in *E. coli* and separated on tricine SDS-PAGE and visualized by Coomassie blue staining (A), or immunodetection with the pooled human serum of Brazil nut allergic patients (B).

FIG. 6 showed the nucleotide and amino acid sequences of the native and modified BNMRP. Specific point mutation was introduced by site-directed mutagenesis using PCR. The nucleotide sequences of the native (BNMRP cDNA) and the modified (mBNMRP cDNA) were aligned. The amino acid sequence of the native BNMRP (BNMRP pro) was shown at the top of the cDNA alignment, and the modified BNMRP (mBNMRP pro) under the cDNA alignment. The specific mutations were highlighted by grayscale background.

The inventors had chosen amino acids in the epitopes that, when changed, resulted in the greatest reduction in IgE binding. As a result, most of the selected amino acids were mutated to alanine. However, 4 arginines encoded by the codon AGG in the cDNA were mutated to methionine. Thus, the methionine content of the modified BNMRP is simultaneously increased from 18 to 22% after mutation. A total of 19 amino acids were modified and the changes were confirmed by sequence analysis. The modified nucleic acid sequence of BNMRP is identified as SEQ ID NO:133.

Through the application of this systematic approach, the present invention demonstrates that the two methionine-rich regions in the large subunit of the illustrating protein of BNMRP possess IgE binding activity and the IgE binding ability of the two epitopes can be reduced or removed by mutation of the arginine rather than the methionine in the epitopes, providing the possibility that a modified target protein with reduced IgE binding ability can be generated by mutations without decreasing its methionine content.

FIG. 7 showed the expression of the native and modified BNMRP in *E. coli*. The cDNA fragments encoding the 12-kDa precursor of the native (BNMRP_12kD) and the modified (mBNMRP_12kD) BNMRP were ligated to the 3' end of the trxA gene in the pET-32a(+) vector, forming constructs expressing fusion proteins containing the native and modified BNMRP (A). The fusion proteins were generated in *E. coli* and separated on tricine SDS-PAGE and stained with Coomassie blue (B). Lane M, protein markers; rBNMRP and rmBNMRP are the fusion proteins containing the native and modified BNMRP, respectively.

The study of recombinant 12-kDa precursors of the original and modified BNMRP expressed in *E. coli* showed that almost all the modified protein was accumulated in the insoluble fraction of the *E. coli* cells, while, in comparison, a portion of the unmodified control protein was in the soluble fraction, as shown in FIG. 7, indicating that the conformational structure of the modified protein, as produced in E. coli, might be different from that of the original form.

EXAMPLE 5

Mutations in BNMRP Reducing its Reactivity with IgE as Reveal in Bacteria Expression After modification, a construct pET-mBNMRP12 was generated for producing the 12-kDa precursor of the modified BNMRP in E. coli as a trxA fusion protein. The recombinant 12-kDa precursors of the original and modified BNMRP expressed in E. coli were purified and separated on tricine-SDS-PAGE and visualized by Coomassie brilliant blue staining.

After separating on a tricine SDS-PAGE, The quantified control and mutant recombinant proteins were electroblotted onto nitrocellulose membrane and probed with the pooled and pre-absorbed Brazil nut allergic patients' serum. On the base of a time course study, the films were found over-developed when the exposure time exceeded 25 minutes as shown in FIG. 8 Comparison of IgE binding activity between the native and modified BNMRP. I, Schematic diagram of the fusion proteins. The 12-kDa precursors of the native (BNMRP_12 kD) and modified (mBNMRP_12 kD) BNMRP were fused to the C-terminus of E. coli thioredoxin (trxA) in pET-32a(+) vector, forming fusion proteins rBNMRP and rmBNMRP, respectively. The fusion proteins were produced in E. coli and purified using Ni-TNA spin column. II, Immunodetection of the native (rBNMRP) and modified (rmBNMRP) BNMRP. One µg of each purified fusion protein, after separated on tricine-SDS PAGEP, was electroblotted onto nitrocellulose membrane and visualized by Ponceau S staining (A). The proteins on the membrane, subsequently, were immunodetected with a pooled serum from 9 patients allergic to Brazil nut. A time course of film development was made, and the films developed in optimal time were presented (B).

FIG. 8(I) showed the schematic diagram of the fusion proteins. The 12-kDa precursors of the native (BNMRP_12 kD) and modified (mBNMRP_12kD) BNMRP were fused to the C-terminus of E. coli thioredoxin (trxA) in pET-32a(+) vector, forming fusion proteins rBNMRP and rmBNMRP, respectively. The fusion proteins were produced in E. coli and purified using Ni-TNA spin column. FIG. 8(II) showed the immunodetection of the native (rBNMRP) and modified (rmBNMRP) BNMRP. One µg of each purified fusion protein, after separated on tricine-SDS PAGEP, was electroblotted onto nitrocellulose membrane and visualized by Ponceau S staining (A). The proteins on the membrane, subsequently, were immunodetected with a pooled serum from 9 patients allergic to Brazil nut and assessed by densitometry scanning and compared with that of the native one. A time course of film development was made, and the films developed in optimal time were presented (B). Analysis showed that the application of the above described modification strategy in the epitopes of BNMRP resulted in a more than 300-fold reduction in the IgE binding of the modified BNMRP.

Through mutating the identified epitope (FIG. 8), the production of modified BNMRP (mBNMRP) with significantly reduced IgE-binding activity and increased methionine content was achieved in this invention.

EXAMPLE 6

Construction of Plant Gene Expression Systems for Accumulation of Foreign Target Proteins with Reduced Allergenicity To achieve a plant expression of the modified BNMRP gene, the inventors have made use of an Agrobacterium binary vector pBI121. It consists of a right border (RB) and a left border (LB) of T-DNA, neomycin phosphotransferase II (NPT II) selectable marker and β-glucurondiase (GUS) screenable marker genes. RB and LB were used to transfer the DNA region in between them to the plant genome. NPT II gene was used to screen the plant transformants in a culture medium containing kanamycin while GUS gene was used to confirm the transformants by an enzyme assay.

The inventors have further extended the objective, by generating 2 more types of variations of the modified BNMR. The first set aims at restoring the C96, C130 and/or C137 in the MBNMRP sequence, by point mutations. The second set is to make use of a winged bean lysine-rich protein (WBLRP) to stabilize the expression of MBNMRP in a plant. In attempting to put the 3 sets of modified BNMRP genes (namely pBI-phas$_{pro}$::MBNMRP::Phas$_{ter}$, pBI-phas$_{pro}$::MBNMRPMC6/7/8/678::Phas$_{ter}$ and pBI-Phas$_{pro}$::BNSP::LRP1::MBNMRP::LRP2::Phas$_{ter}$) into the plant for protein expression, the inventors have made use of a single method to deliver the genes from a pGEM vector to a pBI vector.

BNMRP/MBNMRP Construct

Flanked within the pGEM-BNMRP and pGEM-mBNMRP vectors respectively, the full length BNMRP and mBNMRP genes were released by Acc I digestion. The fragments were ligated separately to an Acc I/Acc I backbone fragment of pTZ-Phas-P53, containing the phaseolin promoter and terminator sequences. The ligated products were transformed into competent DH5α cells for subsequent manipulation. After confirmation by cycle sequencing, the cassetted genes, namely phas$_{pro}$::BNMRP::Phas$_{ter}$ and phas$_{pro}$::mBNMRP::Phas$_{ter}$, were released from the pTZ backbone by Hind III digestions. The cassettes were ligated into a Hind III cut pBI121 vector to become pBI-phas$_{pro}$::mBNMRP::Phas$_{ter}$. The ligated products were again transformed into competent DH5α cells. The copy number of the cassettes inside pBI121 was tested by an Xba I and Apa I combined digestion. A Sca I digestion, on the other hand, was used to test the orientation of the cassettes in the vector. The vectors that contained a single copy of the target cassette and an orientation that is the same as the NPT II and GUS genes were chosen to transform the competent LBA4404 Agrobacterium cells, using 50 mg/L kanamycin and 25 mg/L streptomycin as the selectable markers.

Cysteine-Restoration Constructs

The present invention also extends to further engineered variants, including mBNMRP with cysteine residues restored, and a lysine-rich protein (e.g. WBLRP) fusion, that were constructed and transformed into tobacco for seed-specific expressions, as shown in FIG. 9 and FIG. 10.

Four constructs were made to restore the $6^{th}$ (C94), $7^{th}$ (C130), $8^{th}$ (C137), or all disulfide bond-related cysteines in MBNMRP, aiming at conserving the disulfide bonds as well as the 3D structure and stability of the protein. These constructs were namely MBNMRPMC6, BNMRPMC7, MBNMRPMC8 and MBNMRPMC678, respectively.

To construct MBNMRPMC6, primer-extension PCR was introduced to mutate alanine (C94) back to cysteine. In the first step, pGEM-MBNMRP was used as a template. A 50 µl PCR reaction mixture containing 2 µg genomic DNA template, 1×Taq buffer (Promega), 0.2 mM dNTP, 0.5 µM BNF5 primer, 0.5 µM M6C primer (Table 6) and 5 units Taq DNA polymerase (Promega, 2.5 u/µl) was made to amplify the 5' fragment of MBNMRP gene, and the PCR conditions were as follows: 94° C. for 5 minutes, then 25 cycles of 94° C. for 30 seconds, 58° C. for 30 seconds and 72° C. for 30 seconds, followed by 1 cycle of 72° C. for 7 minutes. Another PCR using M6N and BNF3 primers (Table 6) was set up to amplify the 3' fragment. Both fragments were purified through DNA electrophoresis and gel elution. A second PCR were used to join the two mutated fragments together, achieved by the BNF5 and BNF3 primers (Table 6). The C94-restored MBN-MRP gene was cloned into a pGEM vector (Promega) to form pGEM-MBNMRPMC6 for the sequence analysis. The procedures for further cloning the gene into pTZ and pBI121 vector were similar to that of the MBNMRP construct.

For MBNMRPMC7, BNF5 and M7C, plus BNF3 and M7N (Table 6), were used to mutate A130 to cysteine. The second stage PCR, the cloning into a pGEM vector to form pGEM-MBNMRPMC7 and further construction were similar to MBNMRPMC6.

To make an MBNMRPMC8 gene, a simple PCR was set up instead of using primer-extension PCR. The primers used were BNF5 and M8C (Table 6). The product was cloned into a pGEM vector (pGEM-MBNMRPMC8) for sequencing. Further manipulation was similar to that of the MBNMRP construct.

The pGEM-MBNMRPMC8 was used as a template to restore C94, and the gene was cloned into pGEM to form a pGEM-MBNMRPMC68. After sequence analysis, the pGEM-MBNMRPMC68 was mutated again to restore C130. The gene which now carried all 3 restored cysteines was again cloned into pGEM, forming a pGEM-MBNMRPMC678. After sequencing, the gene was cut by Acc I and cloned into pTZ. Further cloning steps were similar to that in the MBN-MRP construct.

TABLE 6

Primers Used for Plant Expression of Cysteine-restored MBNMRP

| Primers | Sequences (5'-3') |
|---------|-------------------|
| BNF5 | TGGGTCTACATGGCGAAGATTTCA (SEQ ID NO:134) |
| BNF3 | TGGGTATACTCAGAACCCGGCAAT (SEQ ID NO:135) |
| M6N | AGCTGCGCATGCGAAGGATTA (SEQ ID NO:136) |
| M6C | TAATCCTTCGCATGCGCAGCT (SEQ ID NO:137) |
| M7N | CCTTCCGCCTGCAACCTCAGT (SEQ ID NO:138) |
| M7C | ACTGAGGTTGCAGGCGGAAGG (SEQ ID NO:139) |
| M8C | TGGGTATACTCAGAACCCGGCAATGG AGCCACCCATGGGCAT GCCATAGGACTGAG (SEQ ID NO:140) |

WBLRP-Fusion Construct

In this construct, an MBNMRP gene was ligated inside a winged bean lysine-rich protein (WBLRP) gene, and the fusion construct was transformed into plants to produce a BNMRP-WBLRP fusion protein. WBLRP is a seed protein which can stably express in plant seeds in an abundant amount. The inventors made use of its stabilizing effect to enhance the expression MBNMRP.

The fusion gene was cloned from 2 parts. The first part included a DNA sequence encoding for the BNMRP signal peptide and the first 45 amino acids of WBLRP. The second part comprises a sequence coding for the small and large subunits of BNMRP and the remaining 116 amino acids of WBLRP. The two parts were joined by an Xba I site, conferred by the primers LRP1-3Xba and BN5Xba (Table 7), respectively. To clone the two parts, primer-extension PCR method was used. For the first part, BNF5 and SP-LRP3 primers (Table 6) were used to amplify the DNA sequence of BNMRP signal peptide, using pGEM-mBNMRP as a template. The sequence encoding for the N-terminal part of WBLRP was cloned from WBLRP cDNA by SP-LRP5 and LRP1-3Xba primers (Table 7). Both fragments were gel-purified and fused together by another PCR using BNF5 and LRP1-3Xba primers. The product was cloned into a pGEM vector (pGEM-BNSP::LRP1) for sequencing. The second part also involves amplification of two fragments. The first fragment was the BNMRP (Q37 to S139), amplified by BN5-Xba and BNLRP2-3 primers (Table 7). The second fragment was the LRP C-terminal part, amplified by BNLRP2-5 and LRP2-3 primers (Table 7). As in the first part, both fragments were gel-purified and fused together by another PCR using BN5-Xba and LRP2-3 primers. The product was cloned into a pGEM vector (pGEM-BNMRP::LRP2) for sequencing.

The cloned fragments were released from the pGEM vector by Acc I and Xba I digestions. They were gel-purified and ligated into a pTZ-Phas backbone to become a pTZ-Phas$_{pro}$::BNSP::LRP1::BNMRP::LRP2::Phas$_{ter}$. The whole cassette was transformed into a pBI121 (pBI-Phas$_{pro}$::BNSP::LRP1::MBNMRP::LRP2::Phas$_{ter}$) similar to that of MBNMRP.

TABLE 7

Primers Used for Plant Expression of WBLRP-fused MBNMRP

| Primers | Sequences (5'-3') |
|---------|-------------------|
| BNF5 | TGGGTCTACATGGCGAAGATTTCA (SEQ ID NO:141) |
| SP-LRP5 | GGAGGAGAACATGGGTGTTT (SEQ ID NO:142) |
| SP-LRP3 | AAACACCCATGTTCTCCTCC (SEQ ID NO:143) |
| LRP2-3 | TGGGTATACTCAATTGTATTCAGGATG (SEQ ID NO:144) |
| BNLRP2-5 | TGGGTGGCTCCGGAAATGGTGG (SEQ ID NO:145) |
| BNLRP2-3 | CCACCATTTCCGGAGCCACCCA (SEQ ID NO:146) |
| LRP1-3Xba | CTAGTCTAGACTCAACAATTTCAAC (SEQ ID NO:147) |
| BN5Xba | CTAGTCTAGACAGGAGGAGTGTGCC (SEQ ID NO:148) |

FIG. 9 showed the constructs for transforming *Arabidopsis*, tobacco and soybean: bnmrp, coding for native BNMRP; mbnmrp, coding for modified BNMRP; mc6, coding for modified BNMRP with $6^{th}$ cysteine restored; mc7, coding for modified BNMRP with $7^{th}$ cysteine restored; mc8, coding for modified BNMRP with $8^{th}$ cysteine restored; mc678, coding for modified BNMRP with all cysteine residues restored. The restoration of cysteine codons were achieved by overlapping extension PCR method. All constructs were ligated into pBI 121 and transformed into the three host plants.

Tobacco Transformation and Regeneration

Seeds of wild type tobacco (*Nicotiana tabacum* L. cv *Xanthin.* nc) were sterilized in Clorox solution (Sodium hyprochlorite, 5.25%) for 3 minutes by vortexing and shaking, followed by washing in 1 ml sterile distilled water for 1 minute 3 times. Then the sterile seeds were plated on MS medium (4.3 g/L MS salts (Gibco), 1% sucrose, 0.5 g/L MES and 0.8% bacto-agar, pH5.7) in magenta box and allowed to germinate in growth chamber under conditions of 16 hours light/8 hours dark cycles at 25° C. After one month, sterile tobacco leaves were cut from the plant and used for tobacco transformation.

Tobacco transformation was performed using the method of Fisher et al. (1995). A single colony of *Agrobacterium* harboring the chimeric gene construct was inoculated in 3 ml LB medium (10 g/L Bacto peptone, 10 g/L yeast extract and 5 g/L NaCl) containing 25 mg/L streptomycin and 50 mg/L kanamycin. The culture was incubated overnight at 28° C. with shaking (300-350 rpm), until the culture reaching an $OD_{620}>1.0$. Then the culture was spun down and washed with an inoculation medium [4.4 g/L MS salts (Sigma 5519), 3% sucrose, 1 mg/L BA, 0.1 mg/L IAA and 100 µM As, pH5.7] 3 times. The cell pellet was re-suspended in a 3 ml inoculation medium and was ready for tobacco transformation.

Young leaves from one-month-old tobacco were cut into small square discs (0.5×0.5 cm$^2$). Then the discs were immersed in 10× diluted *Agrobacterial* culture for 10 minutes. The discs were first transferred to sterile filter paper for excess *Agrobacterium* removal and then transferred onto solidified co-cultivation medium [42.4 g/L MS salt (Sigma 9274), 1 mg/L BA, 0.1 mg/L IAA and 100 µM As, pH 5.7] for 2 days at 25° C.

After co-cultivation, the discs were transferred onto a selection shooting medium [42.4 g/L MS salt (Sigma 9274), 1 mg/L BA, 0.1 mg/L IAA, 500 mg/L carbenicilin and 100 mg/L kanamycin pH 5.7] and incubated in a growth chamber under a condition of 16 hours light/8 hours dark cycles at 25° C. for callus and shoot formation. After 2-3 weeks, calli were formed on the discs and regenerated shoots were grown out after more than 2 weeks. Then the regenerated shoots were cut off and transferred to a selection rooting medium [4.3 g/L MS salts (Gibco), 3% sucrose, 0.8% agar, pH5.7] for rooting. After 3-4 weeks, the regenerated transgenic tobacco were transferred to soil and grown in a greenhouse for further expression analysis.

FIG. 10 showed the summary of all the constructs that had been transformed into tobacco, in which:

1. pBI-phas$_{pro}$::BNMRP::Phas$_{ter}$
2. pBI-phas$_{pro}$::MBNMRP::Phas$_{ter}$
3. pBI-phas$_{pro}$::MBNMRPMC6::Phas$_{ter}$
4. pBI-phas$_{pro}$::MBNMRPMC7::Phas$_{ter}$
5. pBI-phas$_{pro}$::MBNMRPMC8::Phas$_{ter}$
6. pBI-phas$_{pro}$::MBNMRPMC678::Phas$_{ter}$
7. pBI-Phas$_{pro}$::BNSP::LRP1::MBNMRP::LRP2::Phas$_{ter}$ FIG. 11 showed the regeneration of tobacco after transformation, in which (a) the regenerated tobacco shoots were placed in rooting medium for root regeneration; and (b) the regenerated plants carrying the target genes were planted in greenhouse for immature and mature seeds.

It was found that Calli were formed successfully from the leaf discs under strict hormonal control. The inventors have also been able to regenerate new tobacco plants from these transformed calli and transferred them into soil culture after root formation (FIG. 9 and FIG. 11).

EXAMPLE 7

Detection and Analysis of Plants for Transgene Integration and Expression of Recombinant Proteins with Reduced Negative Allergenic Activity PCR Screening for Gene Integration Genomic DNA was extracted from tobacco leaves using the CTAB protocol of Doyle et al. (1990). Fresh leaves (~100 mg) were placed in an eppendorf tube and treated with liquid nitrogen. Five drops of a CTAB extraction buffer [2% CTAB, 100 mM Tris-HCl (pH 8.0), 1.4M NaCl, 20 mM EDTA and 0.2% β-mercaptoethanol] and a pinch of sterile sand were added into the eppendorf. The leaves were then ground into homogenate with a glass rod. Five hundred µl of the CTAB extraction buffer was added to the homogenate, followed by 60° C. incubation for 30 minutes with periodic mixing. The plant lysate was then mixed gently with 500 µl of chloroform: isoamyl alcohol (24:1, v/v) and centrifuged at 13,000 rpm at 4° C. for 5 minutes. The upper aqueous layer was transferred to a new eppendorf tube and mixed with 330 µl of cold isopropanol. The mixture was then incubated at −20° C. for 1 hour and centrifuged at 13,000 rpm at 4° C. for 15 minutes. The supernatant was discarded and the pellet was washed with 70% ethanol. After centrifugation and removing the ethanol, the pellet was dried under vacuum for 10 minutes at room temperature. The dried DNA pellet was re-suspended in 50 µl TE buffer [10 mM Tris-HCl (pH8.0) and 1 mM EDTA]. The DNA concentration was determined by $OD_{260}$ measurement using a spectrophotometer.

A 50 µl PCR reaction mixture containing 2 µg of a genomic DNA template, 1×Taq buffer (Promega), 0.2 mM dNTP, 0.5 µM of a BNF5 primer, 0.5 µM of a BNF3 primer and 5 units Taq DNA polymerase (Promega, 2.5 µg/µl) was prepared and a PCR condition was set as follows: 94° C. for 5 minutes, then 25 cycles of 94° C. for 30 seconds, 58° C. for 30 seconds and 72° C. for 30 seconds, followed by 1 cycle of 72° C. for 7 minutes. DNA was checked by gel electrophoresis in a 1% agarose/TAE (0.04M Tris-acetate and 1 mM EDTA) gel.

Northern Blot Analysis

Total RNA was extracted from tobacco immature seeds (18-20 days after flowering, DAF) using the method of Altenbach et al. (1989). Fresh developing seeds (~100 mg) were placed in a mortar and ground into fine powder with a pestle by adding liquid nitrogen. Then the powder was transferred to an eppendorf tube and mixed with 0.5 ml of an extraction buffer [0.1M LiCl, 0.1M Tris-HCl (pH8.0), 0.1M EDTA, 1% SDS and 1:1 (v/v) phenol]. The mixture was incubated at 55° C. for 15 minutes with periodic mixing and then mixed with 0.25 ml of chloroform: isoamyl alcohol (24:1, v/v) by vortexing. The mixture was centrifuged at 14,000 rpm for 5 minutes at room temperature. The upper aqueous layer was transferred to a new eppendorf tube and mixed with equal volume of 4M LiCl. The mixture was stored at 4° C. overnight and then centrifuged at 14,000 rpm at 4° C. for 10 minutes. The supernatant was discarded and the pellet was washed with 2M LiCl. After centrifugation and removing the supernatant, the pellet was re-suspended in 0.25 ml DEPC-treated water and then mixed with 25 µl of 3M sodium acetate (pH5.0) and two volumes of 100% ethanol. The mixture was kept at −20° C. for 1 hour and then centrifuged at 14,000 rpm at 4° C. for 30 minutes to obtain the pellet. The pellet was washed with 70% ethanol twice and dried under vacuum for 10 minutes. The dried RNA pellet was re-suspended in 30 µl DEPC $H_2O$. The RNA concentration was determined by $OD_{260}$ measurement using a spectrophotometer.

For each sample, 8 µg of total RNA was separated by the formaldehyde denaturing agarose gel (1% agarose, 1×MOPS, 3% formaldehyde) following the protocol as described by Lehrach (1977). For northern blot analysis, 20×SSC buffer was used as the transfer buffer, and the RNA was blotted from the gel to a positively charged nylon membrane (Roche) by a vacuum method. The WBMRP mRNA was detected in the samples by hybridization with the WBMRP probe (50° C.), and was visualized by using the DIG Nucleic Acid Detection Kit (Boehringer Mannheim).

Using northern blot, the inventors successfully detected transcriptional signals from the transgenic tobacco plants, as shown in FIG. 12. The size of bands in all constructs were about 600-700 bp, except for the fusion construct MBNMRP-WBLRP, which showed larger bands.

Western Blot Analysis

Total seed protein was extracted from 0.05 g of mature tobacco seeds by grinding the seeds into powder and mixing with 1 ml protein extraction buffer [125 mM Tris-HCl, pH7.5, 7.75% SDS, 10% β-mercaptoethanol]. The homogenate was then centrifuged at 14,000 rpm for 15 minutes. The clear supernatant was transferred to a new eppendorf tube and saved as seed total protein extract (STPE).

STPEs (15 µl) extracted were then separated by 16.5% tricine-SDS-PAGE (Schagger and Jagow, 1987). They were mixed with equal volume of 2× sample loading buffer (8% SDS, 24% glycerol, 100 mM Tris-base, 4% β-mercaptoethanol and trace amount of bromophenol blue) and incubated at 99° C. for 10 minutes. The samples were loaded separated by 16.5% tricine-SDS-PAGE. Anode buffer (0.2M Tris-base, pH 8.9) and cathode buffer (0.1M Tris-base, 0.1M Tricine and 0.1% SDS, pH 8.25) were used in the gel electrophoresis. Then the tricine-gel, was equilibrated in Towbin transfer buffer (25 mM Tris, 192 mM glycine, 20% methanol) for 10 minutes. A piece of polyvinylidene difluoride (PVDF) membrane was first treated with 100% methanol for 1 minute and then equilibrated in Towbin transfer buffer for 15 minutes. The proteins in the tricine-gel were blotted onto PVDF membrane by using Trans-blot electrophoretic transfer cell (Bio-Rad). The transfer cell was filled with Towbin transfer buffer and placed in an ice-bath. Electro-transfer was performed at 100V for 1 hour.

After electroblotting, the membrane was subjected to immunodetection using AURORA Western Blot Chermiluminescent Detection System (ICN). The membrane was incubated in blocking buffer (1×PBS, 0.2% Aurora™ blocking reagent and 0.1% Tween-20) for 1 hour and then for another hour in blocking buffer containing 1:5000 anti-MBNMRP polyclonal antibody. Unbound primary antibody was removed by washing the membrane in a blocking buffer for 5 minutes (2 times). Then the membrane was incubated in the blocking buffer with 1:5000 anti-goat IgG secondary antibody-alkaline phosphatase conjugate for 1 hour. Again the unbound secondary antibody was removed by washing the membrane in blocking buffer for 5 minutes (3 times). Then the membrane was washed in assay buffer [20 mM Tris-HCl (pH9.8), 1 mM MgCl$_2$] for 2 minutes (2 times). After adding 1 ml chemiluminescent substrate solution, the membrane was ready for film exposure and development.

The results were showed as in FIG. 13. In (a) and (b), anti-MBNMRP antibodies were used to detect the expression of transgenic seeds. Two bands sized from 13-15 kDa were found in each positive samples. In (c), anti-LRP antibodies were used. The protein band sizes were about 3-35 kDa. Interestingly, the inventors detected two bands with size larger than expected, which may be due to the resistance of the pro-peptides to be modified to mature proteins, after mutation of the MBNMRP sequences.

Simulated Gastric Digestions

Protein was extracted from 0.05 g of mature tobacco seeds by grinding the seeds into powder and mixing with 1 ml of a protein extraction buffer [100 mM Tris-HCl, pH8.9, 0.3M NaCl, 8M Urea, 2% CHAPS]. The homogenates were sonicated for 15 mins, and then centrifuged at 14,000 rpm for 5 minutes. The clear supernatants were transferred to new eppendorfs tube and saved.

Porcine pepsin (Sigma) was weighed and dissolved in simulated gastric fluid (SGF) (0.03M sodium chloride, hydrochloric acid to pH1.2) to a final concentration of 0.04 µg/µl. Digestion mixtures were prepared according to those listed in Table 8. The mixtures were shaken at 37° C. and the digestions were started when pepsin was added. Digestions with different time courses were performed, and the reactions were stopped by adding a quenching solution to neutral pH. The same volume (33 µl) of the sample loading buffer was added to these samples, and tricine-SDS PAGE was used to separate the proteins. For blotting, PVDF membrane and Towbin transfer buffer were used. The immuno-detection was carried out by an AURORA western blot chemiluminescent detection system (ICN), using WBLRP-specific polyclonal antibodies.

TABLE 8

Composition of Pepsin Digestion Mixture

| Components | Amount |
|---|---|
| SGF | 20.4 µl |
| Target Protein (1 µg/µl) | 6 µl |
| Pepsin (0.04 µg/µl) | 6.6 µl |
| Final | 33 µl |

The inventors compared the thermo-stability of MBN-MRP-WBLRP with native BNMRP, and the results showed as in FIG. 14: (a) Native BNMRP protein from Brazil nut and (b) MBNMRP-WBLRP protein. The protein bands of MBN-MRP-LRP were digested within 30 mins, as detected by anti-LRP antibodies. The results suggested that MBNMRP showed a significant decrease in thermo-stability than BNMRP, which may reflect a decrease in allergenic potential.

REFERENCES

1. Altenbach S. B., Kuo C. C., Staraci L. C., Pearson K. W., Wainwright C., Georgescu A. and Townsend J. Accumulation of a Brazil nut albumin in seeds of transgenic canola results in enhanced levels of seed protein methionine. *Plant Mol. Biol.* 18, 235-245 (1992).
2. Altenbach S. B., Pearson K. W., Leung F. W. & Sun S. S. M. Cloning and sequence analysis of a cDNA encoding a Brazil nut protein exceptionally rich in methionine. *Plant Mol. Biol.* 8, 239-250 (1987).
3. Altenbach S. B., Pearson K. W., Meeker G, Staraci L. C. & Sun S. S. M. Enhancement of the methionine content of seed proteins by the expression of a chimeric gene encoding a methionine-rich protein in transgenic plants. *Plant Mol. Biol.* 13, 513-522 (1989).
4. Ampe C., Van Damme J., de Castro L. A., Sampaio M. J., Van Montagu M. & Vandekerckhove J. The amino-acid sequence of the 2S sulfur-rich proteins from seeds of Brazil nut (*Bertholletia excelsa* H.B.K.). *Eur J Biochem.* 159, 597-604 (1986).

5. Aragao F. J., de Sa M. F., Almeida E. R., Gander E. S. & Rech E. L. Particle bombardment-mediated transient expression of a Brazil nut methionine-rich albumin in bean (*Phaseolis vulgaris* L.). *Plant Mol. Biol.* 20, 357-359 (1992).

6. Arshad S. H., Malmberg E., Krapf K. & Hide D. W. Clinical and immunological characteristics of Brazil nut allergy. *Clin Exp Allergy.* 21, 373-376 (1991).

7. Asero R., Mistrello G, Roncarolo D. & Amato S. Allergy to minor allergens of Brazil nut. *Allergy* 57, 1080-1081 (2002).

8. Ayuso R., Lehrer S. B. & Reese G Identification of continuous, allergenic regions of the major shrimp allergen Pen a 1 (tropomyosin). *Int. Arch. Allergy Immunol.* 127, 27-37 (2002).

9. Banerjee B., Kanitpong K., Fink J. N., Zussman M., Sussman G. L., Kelly K. J. & Kurup V P. Unique and shared IgE epitopes of Hev b 1 and Hev b 3 in latex allergy. *Mol. Immunol.* 37, 789-798 (2000).

10. Baerga-Ortiz A., Hughes C. A., Mandell J. G. & Komives E. A. Epitope mapping of a monoclonal antibody against human thrombin by H/D-exchange mass spectrometry reveals selection of a diverse sequence in a highly conserved protein. *Protein Sci.* 11, 1300-1308 (2002).

11. Bannon G. A., Cockrell G. Connaughton C., West C. M., Helm R., Stanley J. S., King N., Rabjohn P., Sampson H. A. & Burks A. W. Engineering, characterization and in vitro efficacy of the major peanut allergens for use in immunotherapy. *Int. Arch. Allergy Immunol.* 124, 70-72 (2001).

12. Bartolome B., Mendez J. D., Armentia A., Vallverdu A. & Palacios R. Allergens from Brazil nut: immunochemical characterization. *Allergol. Immunopathol (Madr).* 25, 135-144 (1997).

13. Bechtold N., Ellis J. & Pelletier G. In planta *Agrobacterium*-mediated gene transfer by infiltration of adult *Arabidopsis thaliana* plants. *C. R. Acad. Sci. Paris, Life Sci.* 316, 1194-1199.

14. Beezhold D. H., Hickey V. L. & Sussman G. L. Mutational analysis of the IgE epitopes in the latex allergen Hev b 5. *J. Allergy Clin. Immunol.* 107, 1069-1076 (2001).

15. Bredehorst R. & David K. What establishes a protein as an allergen? *J. Chromatogr. B* 756, 33-40 (2001).

16. Bufe A. Significance of IgE-binding epitopes in allergic disease. *J. Allergy Clin. Immunol.* 107, 219-221 (2001).

17. Burks A. W., Shin D., Cockrell G. Stanley J. S., Helm R. M. & Bannon G. A. Mapping and mutational analysis of the IgE-binding epitopes on Ara h 1, a legume vicilin protein and a major allergen in peanut hypersensitivity. *Eur. J. Biochem.* 245, 334-339 (1997).

18. Busse P. J., Jarvinen K. M., Vila L., Beyer K. & Sampson H. A. Identification of sequential IgE-binding epitopes on bovine alpha(s2)-casein in cow's milk allergic patients. *Int. Arch. Allergy Immunol.* 129, 93-96 (2002).

19. Chatchatee P., Jarvinen K. M., Bardina L., Beyer K. & Sampson H. A. Identification of IgE- and IgG-binding epitopes on alpha(s1)-casein: differences in patients with persistent and transient cow's milk allergy. *J. Allergy Clin. Immunol.* 107, 379-383 (2001).

20. Chatchatee P., Jarvinen K. M., Bardina L., Vila L., Beyer K. & Sampson H. A. Identification of IgE and IgG binding epitopes on beta- and kappa-casein in cow's milk allergic patients. *Clin. Exp. Allergy* 31, 1256-1262 (2001).

21. Conceicao Ada S., Van Vliet A., Krebbers E. Unexpectedly higher expression levels of a chimeric 2S albumin seed protein transgene from a tandem array construct. *Plant Mol. Biol.* 26, 1001-1005 (1994).

22. Costa M. A., Duro G, Izzo V., Colombo P., Mirisola M. G., Locorotondo G., Cocchiara R. & Geraci D. The IgE-binding epitopes of rPar j 2, a major allergen of *Parietaria judaica* pollen, are heterogeneously recognized among allergic subjects. *Allergy* 55, 246-250 (2000).

23. Doyle, J. D., Doyle, J. J. and Bailey, L. H. 1990. Isolation of plant DNA from fresh tissue. *Focus* 12, 12-15

24. Fisher D. K. & Guiltinan M. J. Rapid, efficient production of homozygous transgenic tobacco plants with *Agrobacterium tumefaciens*: A seed-to-seed protocol. *Plant Mol. Biol.* 13, 278-289 (1995).

25. Gonzalez E. M., Villalba M., Lombardero M., Aalbers M., van Ree R. & Rodriguez R. Influence of the 3D-conformation, glycan component and microheterogeneity on the epitope structure of Ole e 1, the major olive allergen. Use of recombinant isoforms and specific monoclonal antibodies as immunological tools. *Mol. Immunol.* 39, 93-101 (2002).

26. Guerche P, De Almeida E R, Schwarztein M A, Gander E, Krebbers E, Pelletier G Expression of the 2S albumin from *Bertholletia excelsa* in *Brassica napus*. *Mol Gen Genet.* 221, 306-314 (1990).

27. Helm R. M., Cockrell G., Connaughton C., Sampson H. A., Bannon G. A., Beilinson V, Nielsen N. C. & Burks A. W. A soybean G2 glycinin allergen. 2. Epitope mapping and three-dimensional modeling. *Int. Arch. Allergy Immunol.* 123, 213-219 (2000).

28. Helm R. M., Cockrell G. Connaughton C., West C. M., Herman E., Sampson H. A., Bannon G. A. & Burks A. W. Mutational analysis of the IgE-binding epitopes of P34/Gly m Bd 30K. *J. Allergy Clin. Immunol.* 105, 378-384 (2000).

29. Hemmens V. J., Baldo B. A., Underwood P. A., Holen E. & Elsayed S. Common antigenic and allergenic determinants on codfish proteins detected with mouse monoclonal IgG and human IgE antibodies. *Mol. Immunol.* 26, 477-484 (1989).

30. Ho S. N., Hunt H. D., Horton R. M., Pullen J. K. & Pease L. R. Site-directed mutagenesis by overlap extension using the polymerase chain reaction. *Gene* 77, 51-59 (1989).

31. Jarvinen K. M., Chatchatee P., Bardina L., Beyer K. & Sampson H. A. IgE and IgG binding epitopes on alpha-lactalbumin and beta-lactoglobulin in cow's milk allergy. *Int. Arch. Allergy Immunol.* 126, 111-118 (2001).

32. Kahlert H., Petersen A., Becker W. M. & Schlaak M. Epitope analysis of the allergen ovalbumin (Gal d II) with monoclonal antibodies and patients' IgE. *Mol. Immunol.* 29, 1191-1201 (1992).

33. Karisola P., Alenius H., Mikkola J., Kalkkinen N., Helin J., Pentikainen O. T., Repo S., Reunala T., Turjanmaa K., Johnson M. S., Palosuo T. & Kulomaa M. S. The major conformational IgE-binding epitopes of hevein (Hev b 6.02) are identified by a novel chimera-based allergen epitope mapping strategy. *J. Biol. Chem.* 277, 22656-22661 (2002).

34. Lehrach, H., Diamond, D., Wozney, J. M. and Boedtker, H. RNA molecular weight determinations by gel electrophoresis under denaturing conditions, a critical reexamination. *Biochemistry* 16, 4743 (1977).

35. Menendez-Arias L., Dominguez J., Moneo I. & Rodriguez R. Epitope mapping of the major allergen from yellow mustard seeds, Sin a I. *Mol. Immunol.* 27, 143-150 (1990).

36. Menendez-Arias L., Moneo I., Dominguez J. & Rodriguez R. Primary structure of the major allergen of yellow mustard (*Sinapis alba* L.) seed, Sin a 1. *Eur J. Biochem.* 177, 159-166 (1988).

37. Mine Y. & Wei Zhang J. Identification and fine mapping of IgG and IgE epitopes in ovomucoid. *Biochem. Biophys. Res. Commun.* 292, 1070-1074 (2002).
38. Monsalve R. I., Gonzalez de la Pena M. A., Menendez-Arias L., Lopez-Otin C., Villalba M. & Rodriguez R. Characterization of a new oriental-mustard (*Brassica juncea*) allergen, Bra j IE: detection of an allergenic epitope. *Biochem. J.* 293, 625-632 (1993).
39. Nordlee J. A., Taylor S. L., Townsend J. A., Thomas L. A. & Bush R. K. Identification of a Brazil-nut allergen in transgenic soybeans. *N. Engl. J. Med.* 334, 688-692 (1996).
40. Oommen A., Kelly J., Benson A. & Hefle S. Identification of IgE-binding epitopes of the Brazil nut 2S albumin allergen. *J. Allergy Clin. Immunol.* 105 suppl., 134 (2000).
41. Pastorello E. A., Farioli L., Pravettoni V., Ispano M., Conti A., Ansaloni R., Rotondo F., Incorvaia C., Bengtsson A., Rivolta F., Trambaioli C., Previdi M. & Ortolani C. Sensitization to the major allergen of Brazil nut is correlated with the clinical expression of allergy. *J. Allergy Clin. Immunol.* 102, 1021-1027 (1998).
42. Payne P. I. Breeding for protein quantity and protein quality in seed crops. *In Seed Proteins* (ed. Daussant J., Mosse J. & Vaughan J.) 223-253 (Academic Press Inc., London, 1983).
43. Rabjohn P., Helm E. M., Stanley J. S., West C. M., Sampson H. A., Burks A. W. & Bannon G. A. Molecular cloning and epitope analysis of the peanut allergen *Ara h* 3. *J. Clin. Invest.* 103, 535-542 (1999).
44. Reese G., Ayuso R., Carle T. & Lehrer S. B. IgE-binding epitopes of shrimp tropomyosin, the major allergen Pen a 1. *Int. Arch. Allergy Immunol.* 118, 300-301 (1999).
45. Reese G., Ayuso R., Leong-Kee S. M., Plante M. J. & Lehrer S. B. Characterization and identification of allergen epitopes: recombinant peptide libraries and synthetic, overlapping peptides. *J. Chromatogr. B Biomed. Sci. Appl.* 756, 157-163 (2001).
46. Robotham J. M., Teuber S. S., Sathe S. K. & Roux K. H. Linear IgE epitope mapping of the English walnut (*Juglans regia*) major food allergen, Jug r 1. *J. Allergy Clin. Immunol.* 109, 143-149 (2002).
47. Saalbach I., Pickardt T., Machemehl F., Saalbach G, Schieder O. & Muntz K. A chimeric gene encoding the methionine-rich 2S albumin of the Brazil nut (*Bertholletia excelsa* H.B.K.) is stably expressed and inherited in transgenic grain legumes. *Mol. Gen. Genet.* 242, 226-236 (1994).
48. Saalbach G., Rosso M. & Schumann U. The vacuolar targeting signal of the 2S albumin from Brazil nut resides at the C terminus and involves the C-terminal propeptide as an essential element. *Plant Physiol.* 112, 975-985 (1996).
49. Sakaguchi M., Masuda K., Toda M., Inouye S., Yasueda H., Taniguchi Y., Nagoya T., DeBoer D. J. & Tsujimoto H. Analysis of the canine IgE-binding epitope on the major allergen (*Cry j* 1) of Japanese cedar pollen with anti-*Cry j* 1 monoclonal antibodies. *Vet. Immunol. Immunopathol.* 78, 3543 (2001).
50. Schagger H. & Jagow, G. V. Tricine-Sodium Dodecyl Sulfate-Polyacrylamide Gel Electrophoresis for the separation of proteins in the range from 1 to 100 kDa. *Analytical Biochemistry* 166, 368-379 (1987).
51. Schramm G., Bufe A., Petersen A., Haas H., Merget R., Schlaak M. & Becker W. M. Discontinuous IgE-binding epitopes contain multiple continuous epitope regions: results of an epitope mapping on recombinant Hol 1 5, a major allergen from velvet grass pollen. *Clin. Exp. Allergy* 31, 331-341 (2001).
52. Sen M., Kopper R., Pons L., Abraham E. C., Burks A. W. & Bannon G. A. Protein structure plays a critical role in peanut allergen stability and may determine immunodominant IgE-binding epitopes. *J. Immunol.* 169, 882-887 (2002).
53. Shanti K. N., Martin B. M., Nagpal S., Metcalfe D. D. & Rao P. V. Identification of tropomyosin as the major shrimp allergen and characterization of its IgE-binding epitopes. *J. Immunol.* 151, 5354-5363 (1993).
54. Smith A. M. & Chapman M. D. Reduction in IgE binding to allergen variants generated by site-directed mutagenesis: contribution of disulfide bonds to the antigenic structure of the major house dust mite allergen *Der p* 2. *Mol. Immunol.* 33, 399-405 (1996).
55. Soman K. V., Midoro-Horiuti T., Ferreon J. C., Goldblum R. M., Brooks E. G., Kurosky A., Braun W. & Schein C H. Homology modeling and characterization of IgE binding epitopes of mountain cedar allergen Jun a 3. *Biophys. J.* 79, 1601-1609 (2000).
56. Stanley J. S., King N., Burks A. W., Huang S. K., Sampson H., Cockrell G, Helm R. M., West C. M. & Bannon G. A. Identification and mutational analysis of the immunodominant IgE binding epitopes of the major peanut allergen *Ara h* 2. *Arch. Biochem. Biophys.* 342, 244-253 (1997).
57. Sun S. S. M., Altenbach S. B. & Leung F. W. Properties, biosynthesis and processing of a sulfur-rich protein in Brazil nut (*Bertholletia excelsa* H.B.K.). *Eur J Biochem.* 162, 477-483 (1987).
58. Sun S. S. M. & Larkins B. A. Transgenic plants for improving seed storage proteins. In: *Transgenic Plants*, vol. 1., Ed. S. D. Kung and R. Wu. Academic Press, pp.317-372 (1992).
59. Sun S. S. M., Leung F. W. & Tomic J. C. Brazil nut (*Bertholletia excelsa* H. B. K.) proteins: fractionation, composition, and identification of a sulfur-rich protein. *J. Agric. Food Chem.* 35, 232-235 (1987).
60. Suphioglu C., Schappi G, Kenrick J., Levy D., Davies J. M. & O'Hehir R. E. A novel grass pollen allergen mimotope identified by phage display peptide library inhibits allergen-human IgE antibody interaction. *FEBS Lett.* 502, 46-52 (2001).
61. Takai T., Yokota T., Yasue M., Nishiyama C., Yuuki T., Mori A., Okudaira H. & Okumura Y. Engineering of the major house dust mite allergen Der f 2 for allergen-specific immunotherapy. *Nat Biotechnol.* 15, 754-758 (1997).
62. Townsend I. A., Thomas L. A. Factors which influence the *Agrobacterium*-mediated transformation of soybean. *J. Cell Biochem.* Suppl. 18A, 78. abstract (1994).
63. Tu H. M., Godfrey L. W. & Sun S. S. M. Expression of the Brazil nut methionine-rich protein and mutants with increased methionine in transgenic potato. *Plant Mol. Biol.* 37, 829-838 (1998).
64. Vrtala S., Hirtenlehner K., Vangelista L., Pastore A., Eichler H. G., Sperr W. R., Valent P., Ebner C., Kraft D. & Valenta R. Conversion of the major birch pollen allergen, Bet v 1, into two nonanaphylactic T cell epitope-containing fragments: candidates for a novel form of specific immunotherapy. *J. Clin. Invest.* 99, 1673-1681 (1997).
65. Xiang P., Beardslee T. A., Zeece M. G., Markwell J. & Sarath G. Identification and analysis of a conserved immunoglobulin E-binding epitope in soybean G1a and G2a and peanut Ara h 3 glycinins. *Arch. Biochem. Biophys.* 408, 51-57 (2002).

SEQUENCE LISTING

<160> NUMBER OF SEQ ID NOS: 177

<210> SEQ ID NO 1
<211> LENGTH: 24
<212> TYPE: DNA
<213> ORGANISM: Artificial Sequence
<220> FEATURE:
<223> OTHER INFORMATION: BNMRP fragment, position 262-276

<400> SEQUENCE: 1
gccagatctc ccaggcgggg aatg                                          24

<210> SEQ ID NO 2
<211> LENGTH: 27
<212> TYPE: DNA
<213> ORGANISM: Artificial Sequence
<220> FEATURE:
<223> OTHER INFORMATION: BNMRP fragment, position 325-339

<400> SEQUENCE: 2
cggacctcga gcttcgcatc tgcagct                                       27

<210> SEQ ID NO 3
<211> LENGTH: 24
<212> TYPE: DNA
<213> ORGANISM: Artificial Sequence
<220> FEATURE:
<223> OTHER INFORMATION: BNMRP fragment, position 340-354

<400> SEQUENCE: 3
gccagatctg gcttaaggat gatg                                          24

<210> SEQ ID NO 4
<211> LENGTH: 27
<212> TYPE: DNA
<213> ORGANISM: Artificial Sequence
<220> FEATURE:
<223> OTHER INFORMATION: BNMRP fragment, position 403-417

<400> SEQUENCE: 4
cggacctcga gccctcatca tccttcg                                       27

<210> SEQ ID NO 5
<211> LENGTH: 24
<212> TYPE: DNA
<213> ORGANISM: Artificial Sequence
<220> FEATURE:
<223> OTHER INFORMATION: BNMRP fragment, position 418-432

<400> SEQUENCE: 5
gccagatctc tggccgagaa tatc                                          24

<210> SEQ ID NO 6
<211> LENGTH: 27
<212> TYPE: DNA
<213> ORGANISM: Artificial Sequence
<220> FEATURE:
<223> OTHER INFORMATION: BNMRP fragment, position 478-492

<400> SEQUENCE: 6
cggacctcga gcgaacccgg caatgga                                       27

<210> SEQ ID NO 7
<211> LENGTH: 24

-continued

```
<212> TYPE: DNA
<213> ORGANISM: Artificial Sequence
<220> FEATURE:
<223> OTHER INFORMATION: BNMRP fragment, position 163-177

<400> SEQUENCE: 7
gccagatcac aggaggagtg tcgc                                              24

<210> SEQ ID NO 8
<211> LENGTH: 27
<212> TYPE: DNA
<213> ORGANISM: Artificial Sequence
<220> FEATURE:
<223> OTHER INFORMATION: BNMRP fragment, position 232-246

<400> SEQUENCE: 8
cggacctcga gcgctctcct ccatctg                                           27

<210> SEQ ID NO 9
<211> LENGTH: 24
<212> TYPE: DNA
<213> ORGANISM: Artificial Sequence
<220> FEATURE:
<223> OTHER INFORMATION: control primer

<400> SEQUENCE: 9
cagaccatgg ctcgaggtcc gtgc                                              24

<210> SEQ ID NO 10
<211> LENGTH: 28
<212> TYPE: DNA
<213> ORGANISM: Artificial Sequence
<220> FEATURE:
<223> OTHER INFORMATION: control primer

<400> SEQUENCE: 10
ccgggaattc aaacagccct gcgttata                                          28

<210> SEQ ID NO 11
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 11
aaggccatgg ctggaatgga gccgcacatg                                        30

<210> SEQ ID NO 12
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 12
aaggccatgg ctccgcacat gagcgagtgc                                        30

<210> SEQ ID NO 13
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 13
```

-continued aaggccatgg ctagcgagtg ctgcgagcag                                              30

<210> SEQ ID NO 14
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 14
aaggccatgg cttgcgagca gctggagggg                                              30

<210> SEQ ID NO 15
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 15
aaggccatgg ctctggaggg gatggacgag                                              30

<210> SEQ ID NO 16
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 16
aaggccatgg ctatggacga gagctgcaga                                              30

<210> SEQ ID NO 17
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 17
aaggccatgg ctagctgcag atgcgaa                                                 27

<210> SEQ ID NO 18
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 18
aaggccatgg ctatgatgat gatgaggatg                                              30

<210> SEQ ID NO 19
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 19
aaggccatgg ctatgaggat gcaacaggag                                              30

<210> SEQ ID NO 20
<211> LENGTH: 30
<212> TYPE: DNA
<213> ORGANISM: Artificial Sequence

```
<220> FEATURE:
<223> OTHER INFORMATION: primer to construct BNMRP recombinant peptide

<400> SEQUENCE: 20
aaggccatgg ctcaacagga ggagatgcaa                                              30

<210> SEQ ID NO 21
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 21
aaggccatgg ctgagatgca accccgaggg                                              30

<210> SEQ ID NO 22
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 22
aaggccatgg ctccccgagg ggagcagatg                                              30

<210> SEQ ID NO 23
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 23
aaggccatgg ctgagcagat gcgaaggatg                                              30

<210> SEQ ID NO 24
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 24
aaggccatgg ctcgaaggat gatgagg                                                 27

<210> SEQ ID NO 25
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 25
aaggccatgg ctaatatccc ttcccgctgc                                              30

<210> SEQ ID NO 26
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 26
aaggccatgg cttcccgctg caacctcagt                                              30
```

<210> SEQ ID NO 27
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 27
aaggccatgg ctaacctcag tcccatgaga                                       30

<210> SEQ ID NO 28
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 28
aaggccatgg ctcccatgag atgccccatg                                       30

<210> SEQ ID NO 29
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 29
aaggccatgg cttgccccat gggtggctcc                                       30

<210> SEQ ID NO 30
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 30
aaggccatgg ctggtggctc cattgccggg                                       30

<210> SEQ ID NO 31
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 31
aaggccatgg ctctcagcca ctgccggatg                                       30

<210> SEQ ID NO 32
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 32
aaggccatgg cttgccggat gtacatgaga                                       30

<210> SEQ ID NO 33
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 33
aaggccatgg cttacatgag acagcagatg                                    30

<210> SEQ ID NO 34
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 34
aaggccatgg ctcagcagat ggaggagagc                                    30

<210> SEQ ID NO 35
<211> LENGTH: 30
<212> TYPE: DNA
<213> ORGANISM: Artificial Sequence
<220> FEATURE:
<223> OTHER INFORMATION: primer to construct BNMRP recombinant peptide

<400> SEQUENCE: 35
aaggccatgg ctgaggagag cccgtaccag                                    30

<210> SEQ ID NO 36
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 36
ttggaattct tattcgcatc tgcagca                                       27

<210> SEQ ID NO 37
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 37
ttggaattct tagcagctct cgtccat                                       27

<210> SEQ ID NO 38
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 38
ttggaattct tagtccatcc cctccag                                       27

<210> SEQ ID NO 39
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 39
ttggaattct tactccagct gctcgca                                       27

<210> SEQ ID NO 40

```
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 40
ttggaattct tactcgcagc actcgct                                              27

<210> SEQ ID NO 41
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 41
ttggaattct tactcgctca tgtgcgg                                              27

<210> SEQ ID NO 42
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 42
ttggaattct tagtgcggct ccattcc                                              27

<210> SEQ ID NO 43
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 43
ttggaattct tacctcatca tccttcg                                              27

<210> SEQ ID NO 44
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 44
ttggaattct taccttcgca tctgctc                                              27

<210> SEQ ID NO 45
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 45
ttggaattct tactgctccc ctcgggg                                              27

<210> SEQ ID NO 46
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 46
```
ttggaattct tatcggggtt gcatctc                                            27

<210> SEQ ID NO 47
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 47
ttggaattct tacatctcct cctgttg                                            27

<210> SEQ ID NO 48
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 48
ttggaattct tactgttgca tcctcat                                            27

<210> SEQ ID NO 49
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 49
ttggaattct tacctcatca tcatcat                                            27

<210> SEQ ID NO 50
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 50
ttggaattct tacatcatcc ttaagcc                                            27

<210> SEQ ID NO 51
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 51
ttggaattct tagaacccgg caatgga                                            27

<210> SEQ ID NO 52
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 52
ttggaattct taaatggagc cacccat                                            27

<210> SEQ ID NO 53
<211> LENGTH: 27
<212> TYPE: DNA

```
<213> ORGANISM: Artificial Sequence
<220> FEATURE:
<223> OTHER INFORMATION: primer to construct BNMRP recombinant peptide

<400> SEQUENCE: 53
ttggaattct taacccatgg ggcatct                                          27

<210> SEQ ID NO 54
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 54
ttggaattct tagcatctca tgggact                                          27

<210> SEQ ID NO 55
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 55
ttggaattct tagggactga ggttgca                                          27

<210> SEQ ID NO 56
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 56
ttggaattct tagttgcagc gggaagg                                          27

<210> SEQ ID NO 57
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 57
ttggaattct taggaaggga tattctc                                          27

<210> SEQ ID NO 58
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 58
ttggaattct taattctcgg ccagcct                                          27

<210> SEQ ID NO 59
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 59
ttggaattct tacatggtct ggtacgg                                          27
```

-continued

```
<210> SEQ ID NO 60
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 60
ttggaattct tagtacgggc tctcctc                                      27

<210> SEQ ID NO 61
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 61
ttggaattct tactcctcca tctgctg                                      27

<210> SEQ ID NO 62
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 62
ttggaattct tactgctgtc tcatgta                                      27

<210> SEQ ID NO 63
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 63
ttggaattct tacatgtaca tccggca                                      27

<210> SEQ ID NO 64
<211> LENGTH: 27
<212> TYPE: DNA
<213> ORGANISM: Artificial Sequence
<220> FEATURE:
<223> OTHER INFORMATION: primer to construct BNMRP recombinant peptide

<400> SEQUENCE: 64
ttggaattct taccggcagt ggctgag                                      27

<210> SEQ ID NO 65
<211> LENGTH: 21
<212> TYPE: DNA
<213> ORGANISM: Artificial Sequence
<220> FEATURE:
<223> OTHER INFORMATION: control primer

<400> SEQUENCE: 65
ttggaattct taagccatgg c                                            21

<210> SEQ ID NO 66
<211> LENGTH: 13
<212> TYPE: PRT
<213> ORGANISM: Artificial Sequence
<220> FEATURE:
```

<223> OTHER INFORMATION: BNMRP deletion set

<400> SEQUENCE: 66

Gln Glu Glu Cys Arg Glu Gln Met Gln Arg Gln Gln Met
1               5                   10

<210> SEQ ID NO 67
<211> LENGTH: 8
<212> TYPE: PRT
<213> ORGANISM: Artificial Sequence
<220> FEATURE:
<223> OTHER INFORMATION: BNMRP deletion set

<400> SEQUENCE: 67

Met Asp Glu Ser Cys Arg Cys Glu
1               5

<210> SEQ ID NO 68
<211> LENGTH: 7
<212> TYPE: PRT
<213> ORGANISM: Artificial Sequence
<220> FEATURE:
<223> OTHER INFORMATION: BNMRP deletion set

<400> SEQUENCE: 68

Gly Gly Ser Ile Ala Gly Phe
1               5

<210> SEQ ID NO 69
<211> LENGTH: 6
<212> TYPE: PRT
<213> ORGANISM: Artificial Sequence
<220> FEATURE:
<223> OTHER INFORMATION: binding domain of the C-terminal fragment of
      the large subunit to IgE

<400> SEQUENCE: 69

Pro Met Arg Cys Pro Met
1               5

<210> SEQ ID NO 70
<211> LENGTH: 10
<212> TYPE: PRT
<213> ORGANISM: Artificial Sequence
<220> FEATURE:
<223> OTHER INFORMATION: IgE binding domain to epitope L4

<400> SEQUENCE: 70

```
Pro Arg Gly Glu Gln Arg Arg Met Met Arg
 1               5                  10
```

<210> SEQ ID NO 71
<211> LENGTH: 4
<212> TYPE: PRT
<213> ORGANISM: Artificial Sequence
<220> FEATURE:
<223> OTHER INFORMATION: IgE binding domain to epitope L6

<400> SEQUENCE: 71

```
Pro Met Arg Cys
 1
```

<210> SEQ ID NO 72
<211> LENGTH: 13
<212> TYPE: PRT
<213> ORGANISM: Artificial Sequence
<220> FEATURE:

<223> OTHER INFORMATION: L4 epitope

<400> SEQUENCE: 72

Glu Met Gln Pro Arg Gly Glu Gln Arg Arg Met Met Arg
 1               5                   10

<210> SEQ ID NO 73
<211> LENGTH: 28
<212> TYPE: DNA
<213> ORGANISM: Artificial Sequence
<220> FEATURE:
<223> OTHER INFORMATION: Primer Used for Alanine Substitution Analysis
      of BNMRP Epitopes

<400> SEQUENCE: 73
cttacatgta catccggcat gcgctgag                                    28

<210> SEQ ID NO 74
<211> LENGTH: 28
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 74
cttacatgta catccgtgcg tggctgag                                    28

<210> SEQ ID NO 75
<211> LENGTH: 27
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 75
cttacatgta cattgcgcat tggctga                                     27

<210> SEQ ID NO 76
<211> LENGTH: 25
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 76
cttacatgta agcccggcat tggct                                       25

<210> SEQ ID NO 77
<211> LENGTH: 22
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 77
cttacattgc catccggcat tg                                          22

<210> SEQ ID NO 78
<211> LENGTH: 22
<212> TYPE: DNA
<213> ORGANISM: Artificial Sequence
<220> FEATURE:
<223> OTHER INFORMATION: Primers Used for Alanine Substitution Analysis of BNMRP Epitopes

<400> SEQUENCE: 78
cttatgcgta catccggcat tg                                              22

<210> SEQ ID NO 79
<211> LENGTH: 34
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 79
cttactcctc catctgctgt ctcattgcag ccat                                 34

<210> SEQ ID NO 80
<211> LENGTH: 31
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 80
cttactcctc catctgctgt cttgcgtaag c                                    31

<210> SEQ ID NO 81
<211> LENGTH: 28
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 81
cttactcctc catctgctgt gccatgta                                        28

<210> SEQ ID NO 82
<211> LENGTH: 28
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 82
cttactcctc catctgtgct ctcatgta                                        28

<210> SEQ ID NO 83
<211> LENGTH: 25
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 83
cttactcctc catcgcctgt ctcat                                           25

<210> SEQ ID NO 84
<211> LENGTH: 25
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 84
cttactcctc agcctgctgt ctcat                                    25

<210> SEQ ID NO 85
<211> LENGTH: 28
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 85
cttacctcat catcatcatc gctaagcc                                 28

<210> SEQ ID NO 86
<211> LENGTH: 28
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 86
cttacctcat catcatcgcc cttaagcc                                 28

<210> SEQ ID NO 87
<211> LENGTH: 28
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 87
cttacctcat catcgccatc cttaagcc                                 28

<210> SEQ ID NO 88
<211> LENGTH: 25
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 88
cttacctcat cgccatcatc cttaa                                    25

<210> SEQ ID NO 89
<211> LENGTH: 22
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 89
cttacctcgc catcatcatc ct                                       22

<210> SEQ ID NO 90
<211> LENGTH: 22
<212> TYPE: DNA
<213> ORGANISM: Artificial Sequence
<220> FEATURE:
<223> OTHER INFORMATION: Primers Used for Alanine Substitution Analysis
      of BNMRP Epitopes

```
<400> SEQUENCE: 90
cttacgccat catcatcatc ct                                              22

<210> SEQ ID NO 91
<211> LENGTH: 28
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 91
cttactgttg catcctcatc gccatcat                                        28

<210> SEQ ID NO 92
<211> LENGTH: 28
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 92
cttactgttg catcctcgcc atcatcat                                        28

<210> SEQ ID NO 93
<211> LENGTH: 28
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 93
cttactgttg catcgccatc atcatcat                                        28

<210> SEQ ID NO 94
<211> LENGTH: 24
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 94
cttactgttg cgccctcatc atca                                            24

<210> SEQ ID NO 95
<211> LENGTH: 21
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 95
cttactgtgc catcctcatc a                                               21

<210> SEQ ID NO 96
<211> LENGTH: 25
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 96
```

-continued

```
cttaccttcg catctgcgcc cctcg                                          25

<210> SEQ ID NO 97
<211> LENGTH: 25
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 97
cttaccttcg catcgcctcc cctcg                                          25

<210> SEQ ID NO 98
<211> LENGTH: 25
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 98
cttaccttcg cgcctgctcc cctcg                                          25

<210> SEQ ID NO 99
<211> LENGTH: 25
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 99
cttaccttgc catctgctcc cctcg                                          25

<210> SEQ ID NO 100
<211> LENGTH: 22
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 100
cttacgctcg catctgctcc cc                                             22

<210> SEQ ID NO 101
<211> LENGTH: 31
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 101
cttactcggc cagcctcatc atcgctcgag c                                   31

<210> SEQ ID NO 102
<211> LENGTH: 28
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 102
```

-continued

```
cttactcggc cagcctcatc gcccttcg                                    28

<210> SEQ ID NO 103
<211> LENGTH: 28
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 103
cttactcggc cagcctcgcc atccttcg                                    28

<210> SEQ ID NO 104
<211> LENGTH: 28
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 104
cttactcggc cagcgccatc atccttcg                                    28

<210> SEQ ID NO 105
<211> LENGTH: 28
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 105
cttactcggc cgccctcatc atccttcg                                    28

<210> SEQ ID NO 106
<211> LENGTH: 28
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 106
cttactccat cagcctcatc atccttcg                                    28

<210> SEQ ID NO 107
<211> LENGTH: 25
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 107
cttagcatct catgggagcg aggtt                                       25

<210> SEQ ID NO 108
<211> LENGTH: 25
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 108
cttagcatct catggcactg aggtt                                       25
```

-continued

<210> SEQ ID NO 109
<211> LENGTH: 25
<212> TYPE: DNA
<213> ORGANISM: Artificial Sequence
<220> FEATURE:
<223> OTHER INFORMATION: Primers Used for Alanine Substitution Analysis
      of BNMRP Epitopes

<400> SEQUENCE: 109
cttagcatct agcgggactg aggtt 25

<210> SEQ ID NO 110
<211> LENGTH: 25
<212> TYPE: DNA
<213> ORGANISM: Artificial Sequence
<220> FEATURE:
<223> OTHER INFORMATION: Primers Used for Alanine Substitution Analysis of BNMRP Epitopes

<400> SEQUENCE: 110
cttagcatgc catgggactg aggtt 25

<210> SEQ ID NO 111
<211> LENGTH: 25
<212> TYPE: DNA
<213> ORGANISM: Artificial Sequence
<220> FEATURE:
<223> OTHER INFORMATION: Primers Used for Alanine Substitution Analysis of BNMRP Epitopes

<400> SEQUENCE: 111
cttaggctct catgggactg aggtt 25

<210> SEQ ID NO 112
<211> LENGTH: 5
<212> TYPE: PRT
<213> ORGANISM: Artificial Sequence
<220> FEATURE:
<223> OTHER INFORMATION: Deletion Epitope of BNMRP

<400> SEQUENCE: 112

Tyr Met Arg Gln Gln
1 5

<210> SEQ ID NO 113
<211> LENGTH: 6
<212> TYPE: PRT
<213> ORGANISM: Artificial Sequence
<220> FEATURE:
<223> OTHER INFORMATION: Deletion Epitope of BNMRP

<400> SEQUENCE: 113

Glu Met Gln Pro Arg Gly
1 5

<210> SEQ ID NO 114
<211> LENGTH: 14
<212> TYPE: PRT
<213> ORGANISM: Artificial Sequence
<220> FEATURE:
<223> OTHER INFORMATION: Epitopes for IgE Binding

<400> SEQUENCE: 114

Leu Ser His Cys Arg Met Tyr Met Arg Gln Gln Met Glu Glu
1 5 10

```
<210> SEQ ID NO 115
<211> LENGTH: 11
<212> TYPE: PRT
<213> ORGANISM: Artificial Sequence
<220> FEATURE:
<223> OTHER INFORMATION: Epitopes for IgE Binding

<400> SEQUENCE: 115

Gly Leu Arg Met Met Met Met Arg Met Gln Gln
  1               5                  10

<210> SEQ ID NO 116
<211> LENGTH: 17
<212> TYPE: PRT
<213> ORGANISM: Artificial Sequence
<220> FEATURE:
<223> OTHER INFORMATION: Epitopes for IgE Binding

<400> SEQUENCE: 116

Glu Met Gln Pro Arg Gly Glu Gln Met Arg Arg Met Met Arg Leu Ala
  1               5                  10                  15

Glu

<210> SEQ ID NO 117
<211> LENGTH: 7
<212> TYPE: PRT
<213> ORGANISM: Artificial Sequence
<220> FEATURE:
<223> OTHER INFORMATION: Epitopes for IgE Binding

<400> SEQUENCE: 117

Asn Leu Ser Pro Met Arg Cys
  1               5

<210> SEQ ID NO 118
<211> LENGTH: 27
<212> TYPE: DNA
<213> ORGANISM: Artificial Sequence
<220> FEATURE:
<223> OTHER INFORMATION: primer for precursor of mBNMRP

<400> SEQUENCE: 118
catgccatgg ctcaggagga gtgtgcc                                      27

<210> SEQ ID NO 119
<211> LENGTH: 27
<212> TYPE: DNA
<213> ORGANISM: Artificial Sequence
<220> FEATURE:
<223> OTHER INFORMATION: primer for precursor of mBNMRP

<400> SEQUENCE: 119
tgggaattct tagaacccgg caatgga                                      27

<210> SEQ ID NO 120
<211> LENGTH: 24
<212> TYPE: DNA
<213> ORGANISM: Artificial Sequence
<220> FEATURE:
<223> OTHER INFORMATION: primer for site directed mutagenesis of BNMRP

<400> SEQUENCE: 120
tgggtctaca tggcgaagat ttca                                         24

<210> SEQ ID NO 121
```

```
<210> SEQ ID NO 121
<211> LENGTH: 24
<212> TYPE: DNA
<213> ORGANISM: Artificial Sequence
<220> FEATURE:
<223> OTHER INFORMATION: primer for site directed mutagenesis of BNMRP

<400> SEQUENCE: 121
tgggtatact cagaacccgg caat                                          24

<210> SEQ ID NO 122
<211> LENGTH: 33
<212> TYPE: DNA
<213> ORGANISM: Artificial Sequence
<220> FEATURE:
<223> OTHER INFORMATION: primer for site directed mutagenesis of BNMRP

<400> SEQUENCE: 122
ctcagccact gcgcgatggc catggcacag cag                                33

<210> SEQ ID NO 123
<211> LENGTH: 36
<212> TYPE: DNA
<213> ORGANISM: Artificial Sequence
<220> FEATURE:
<223> OTHER INFORMATION: primer for site directed mutagenesis of BNMRP

<400> SEQUENCE: 123
ggattaatga tgatgatgat gatgatggca caggag                             36

<210> SEQ ID NO 124
<211> LENGTH: 27
<212> TYPE: DNA
<213> ORGANISM: Artificial Sequence
<220> FEATURE:
<223> OTHER INFORMATION: primer for site directed mutagenesis of BNMRP

<400> SEQUENCE: 124
cattaatcct tcggctgcgc agctctc                                       27

<210> SEQ ID NO 125
<211> LENGTH: 30
<212> TYPE: DNA
<213> ORGANISM: Artificial Sequence
<220> FEATURE:
<223> OTHER INFORMATION: primer for site directed mutagenesis of BNMRP

<400> SEQUENCE: 125
cataggactg aggttggcgg cggaagggat                                    30

<210> SEQ ID NO 126
<211> LENGTH: 30
<212> TYPE: DNA
<213> ORGANISM: Artificial Sequence
<220> FEATURE:
<223> OTHER INFORMATION: primer for site directed mutagenesis of BNMRP

<400> SEQUENCE: 126
acccatgggg gctgccatag gactgaggtt                                    30

<210> SEQ ID NO 127
<211> LENGTH: 33
<212> TYPE: DNA
<213> ORGANISM: Artificial Sequence
<220> FEATURE:
<223> OTHER INFORMATION: primer for site directed mutagenesis of BNMRP

<400> SEQUENCE: 127
```
gagtgtgccg agcagatgca ggcacagcag atg                              33

<210> SEQ ID NO 128
<211> LENGTH: 33
<212> TYPE: DNA
<213> ORGANISM: Artificial Sequence
<220> FEATURE:
<223> OTHER INFORMATION: primer for site directed mutagenesis of BNMRP

<400> SEQUENCE: 128
ctgctgtgcc tgcatctgct cggcacactc ctc                              33

<210> SEQ ID NO 129
<211> LENGTH: 24
<212> TYPE: DNA
<213> ORGANISM: Artificial Sequence
<220> FEATURE:
<223> OTHER INFORMATION: primer for site directed mutagenesis of BNMRP

<400> SEQUENCE: 129
accatgcccg cggcgggaat ggag                                        24

<210> SEQ ID NO 130
<211> LENGTH: 24
<212> TYPE: DNA
<213> ORGANISM: Artificial Sequence
<220> FEATURE:
<223> OTHER INFORMATION: primer for site directed mutagenesis of BNMRP

<400> SEQUENCE: 130
ctccattccc gccgcgggca tggt                                        24

<210> SEQ ID NO 131
<211> LENGTH: 33
<212> TYPE: DNA
<213> ORGANISM: Artificial Sequence
<220> FEATURE:
<223> OTHER INFORMATION: primer for site directed mutagenesis of BNMRP

<400> SEQUENCE: 131
gagcagatgg caatgatgat gatgctggcc gag                              33

<210> SEQ ID NO 132
<211> LENGTH: 33
<212> TYPE: DNA
<213> ORGANISM: Artificial Sequence
<220> FEATURE:
<223> OTHER INFORMATION: primer for site directed mutagenesis of BNMRP

<400> SEQUENCE: 132
ctcggccagc atcatcatca ttgccatctg ctc                              33

<210> SEQ ID NO 133
<211> LENGTH: 441
<212> TYPE: DNA
<213> ORGANISM: Artificial Sequence
<220> FEATURE:
<223> OTHER INFORMATION: modified nucleic acid sequence of BNMRP

<400> SEQUENCE: 133
atggcgaaga tttcagttgc ggcagcagcc ctccttgtcc tcatggccct cggccacgcc     60
accgccttcc gggccaccgt caccaccaca gtggtggagg aggagaacca ggaggagtgt    120
gccgagcaga tgcaggcaca gcagatgctc agccactgcg cgatggccat ggcacagcag    180

```
atggaggaga gcccgtacca gaccatgccc gcggcgggaa tggagccgca catgagcgag      240
tgctgcgagc agctggaggg gatggacgag agctgcgcag ccgaaggatt aatgatgatg      300
atgatgatga tggcacagga ggagatgcaa ccccgagggg agcagatgcc attgatgatg      360
atgctggccg agaatatccc ttccgccgcc aacctcagtc ctatggcagc ccccatgggt      420
ggctccattg ccgggttctg a                                                441
```

```
<210> SEQ ID NO 134
<211> LENGTH: 24
<212> TYPE: DNA
<213> ORGANISM: Artificial Sequence
<220> FEATURE:
<223> OTHER INFORMATION: Primer Used for Plant Expression of
      Cysteine-restored MBNMRP

<400> SEQUENCE: 134
tgggtctaca tggcgaagat ttca                                              24

<210> SEQ ID NO 135
<211> LENGTH: 24
<212> TYPE: DNA
<213> ORGANISM: Artificial Sequence
<220> FEATURE:
<223> OTHER INFORMATION: Primer Used for Plant Expression of
      Cysteine-restored MBNMRP

<400> SEQUENCE: 135
tgggtatact cagaacccgg caat                                              24

<210> SEQ ID NO 136
<211> LENGTH: 21
<212> TYPE: DNA
<213> ORGANISM: Artificial Sequence
<220> FEATURE:
<223> OTHER INFORMATION: Primer Used for Plant Expression of
      Cysteine-restored MBNMRP

<400> SEQUENCE: 136
agctgcgcat gcgaaggatt a                                                 21

<210> SEQ ID NO 137
<211> LENGTH: 21
<212> TYPE: DNA
<213> ORGANISM: Artificial Sequence
<220> FEATURE:
<223> OTHER INFORMATION: Primer Used for Plant Expression of
      Cysteine-restored MBNMRP

<400> SEQUENCE: 137
taatccttcg catgcgcagc t                                                 21

<210> SEQ ID NO 138
<211> LENGTH: 21
<212> TYPE: DNA
<213> ORGANISM: Artificial Sequence
<220> FEATURE:
<223> OTHER INFORMATION: Primer Used for Plant Expression of
      Cysteine-restored MBNMRP

<400> SEQUENCE: 138
ccttccgcct gcaacctcag t                                                 21

<210> SEQ ID NO 139
<211> LENGTH: 21
<212> TYPE: DNA
```

```
<213> ORGANISM: Artificial Sequence
<220> FEATURE:
<223> OTHER INFORMATION: Primer Used for Plant Expression of
      Cysteine-restored MBNMRP

<400> SEQUENCE: 139
actgaggttg caggcggaag g                                              21

<210> SEQ ID NO 140
<211> LENGTH: 57
<212> TYPE: DNA
<213> ORGANISM: Artificial Sequence
<220> FEATURE:
<223> OTHER INFORMATION: Primer Used for Plant Expression of
      Cysteine-restored MBNMRP

<400> SEQUENCE: 140
tgggtatact cagaacccgg caatggagcc acccatgggg catgccatag gactgag       57

<210> SEQ ID NO 141
<211> LENGTH: 24
<212> TYPE: DNA
<213> ORGANISM: Artificial Sequence
<220> FEATURE:
<223> OTHER INFORMATION: Primer Used for Plant Expression of WBLRP-fused
      MBNMRP

<400> SEQUENCE: 141
tgggtctaca tggcgaagat ttca                                           24

<210> SEQ ID NO 142
<211> LENGTH: 20
<212> TYPE: DNA
<213> ORGANISM: Artificial Sequence
<220> FEATURE:
<223> OTHER INFORMATION: Primer Used for Plant Expression of WBLRP-fused
      MBNMRP

<400> SEQUENCE: 142
ggaggagaac atgggtgttt                                                20

<210> SEQ ID NO 143
<211> LENGTH: 20
<212> TYPE: DNA
<213> ORGANISM: Artificial Sequence
<220> FEATURE:
<223> OTHER INFORMATION: Primer Used for Plant Expression of WBLRP-fused
      MBNMRP

<400> SEQUENCE: 143
aaacacccat gttctcctcc                                                20

<210> SEQ ID NO 144
<211> LENGTH: 27
<212> TYPE: DNA
<213> ORGANISM: Artificial Sequence
<220> FEATURE:
<223> OTHER INFORMATION: Primer Used for Plant Expression of WBLRP-fused
      MBNMRP

<400> SEQUENCE: 144
tgggtatact caattgtatt caggatg                                        27

<210> SEQ ID NO 145
<211> LENGTH: 22
<212> TYPE: DNA
<213> ORGANISM: Artificial Sequence
```

-continued

<220> FEATURE:
<223> OTHER INFORMATION: Primer Used for Plant Expression of WBLRP-fused
      MBNMRP

<400> SEQUENCE: 145
tgggtggctc cggaaatggt gg 22

<210> SEQ ID NO 146
<211> LENGTH: 22
<212> TYPE: DNA
<213> ORGANISM: Artificial Sequence
<220> FEATURE:
<223> OTHER INFORMATION: Primer Used for Plant Expression of WBLRP-fused
      MBNMRP

<400> SEQUENCE: 146
ccaccatttc cggagccacc ca 22

<210> SEQ ID NO 147
<211> LENGTH: 25
<212> TYPE: DNA
<213> ORGANISM: Artificial Sequence
<220> FEATURE:
<223> OTHER INFORMATION: Primer Used for Plant Expression of WBLRP-fused
      MBNMRP

<400> SEQUENCE: 147
ctagtctaga ctcaacaatt tcaac 25

<210> SEQ ID NO 148
<211> LENGTH: 25
<212> TYPE: DNA
<213> ORGANISM: Artificial Sequence
<220> FEATURE:
<223> OTHER INFORMATION: Primer Used for Plant Expression of WBLRP-fused
      MBNMRP

<400> SEQUENCE: 148
ctagtctaga caggaggagt gtgcc 25

<210> SEQ ID NO 149
<211> LENGTH: 8
<212> TYPE: PRT
<213> ORGANISM: Artificial Sequence
<220> FEATURE:
<223> OTHER INFORMATION: BNMRP epitope

<400> SEQUENCE: 149

Cys Arg Met Tyr Met Arg Gln Gln
1               5

<210> SEQ ID NO 150
<211> LENGTH: 8
<212> TYPE: PRT
<213> ORGANISM: Artificial Sequence
<220> FEATURE:
<223> OTHER INFORMATION: BNMRP epitope

<400> SEQUENCE: 150

Pro Arg Arg Gly Met Glu Pro His
1               5

<210> SEQ ID NO 151
<211> LENGTH: 9
<212> TYPE: PRT
<213> ORGANISM: Artificial Sequence
<220> FEATURE:

<223> OTHER INFORMATION: BNMRP epitope

<400> SEQUENCE: 151

Arg Met Met Met Met Arg Met Gln Gln
1               5

<210> SEQ ID NO 152
<211> LENGTH: 14
<212> TYPE: PRT
<213> ORGANISM: Artificial Sequence
<220> FEATURE:
<223> OTHER INFORMATION: BNMRP epitope

<400> SEQUENCE: 152

Glu Met Gln Pro Arg Gly Glu Gln Met Arg Arg Met Met Arg
1               5                   10

<210> SEQ ID NO 153
<211> LENGTH: 7
<212> TYPE: PRT
<213> ORGANISM: Artificial Sequence
<220> FEATURE:
<223> OTHER INFORMATION: BNMRP epitope

<400> SEQUENCE: 153

Asn Ile Pro Ser Arg Cys Asn
1               5

<210> SEQ ID NO 154
<211> LENGTH: 4
<212> TYPE: PRT
<213> ORGANISM: Artificial Sequence
<220> FEATURE:
<223> OTHER INFORMATION: BNMRP epitope

<400> SEQUENCE: 154

Pro Met Arg Cys
1

<210> SEQ ID NO 155
<211> LENGTH: 26
<212> TYPE: PRT
<213> ORGANISM: Artificial Sequence
<220> FEATURE:
<223> OTHER INFORMATION: BNMRP epitope

<400> SEQUENCE: 155

Gly Leu Arg Met Met Met Met Arg Met Gln Gln Glu Glu Met Trp Pro
1               5                   10                  15

Arg Gly Glu Trp Met Arg Arg Met Met Arg
            20                  25

<210> SEQ ID NO 156
<211> LENGTH: 25
<212> TYPE: PRT
<213> ORGANISM: Artificial Sequence
<220> FEATURE:
<223> OTHER INFORMATION: BNMRP epitope

<400> SEQUENCE: 156

Leu Ala Glu Asn Ile Pro Ser Arg Cys Asn Leu Ser Pro Arg Met Cys
1               5                   10                  15

Pro Met Gly Gly Ser Ile Ala Gly Phe
            20                  25

```
<210> SEQ ID NO 157
<211> LENGTH: 26
<212> TYPE: PRT
<213> ORGANISM: Artificial Sequence
<220> FEATURE:
<223> OTHER INFORMATION: BNMRP epitope

<400> SEQUENCE: 157

Pro Arg Arg Gly Met Glu Pro His Met Ser Glu Cys Cys Glu Gln Leu
 1               5                  10                  15

Glu Gly Met Asp Glu Ser Cys Arg Cys Glu
            20                  25

<210> SEQ ID NO 158
<211> LENGTH: 26
<212> TYPE: PRT
<213> ORGANISM: Artificial Sequence
<220> FEATURE:
<223> OTHER INFORMATION: BNMRP epitope

<400> SEQUENCE: 158

Gly Leu Arg Met Met Met Met Arg Met Gln Gln Glu Glu Met Gln Pro
 1               5                  10                  15

Arg Gly Glu Gln Met Arg Arg Met Met Arg
            20                  25

<210> SEQ ID NO 159
<211> LENGTH: 25
<212> TYPE: PRT
<213> ORGANISM: Artificial Sequence
<220> FEATURE:
<223> OTHER INFORMATION: BNMRP epitope

<400> SEQUENCE: 159

Leu Ala Glu Asn Ile Pro Ser Arg Cys Asn Leu Ser Pro Met Arg Cys
 1               5                  10                  15

Pro Met Gly Gly Ser Ile Ala Gly Phe
            20                  25

<210> SEQ ID NO 160
<211> LENGTH: 33
<212> TYPE: PRT
<213> ORGANISM: Artificial Sequence
<220> FEATURE:
<223> OTHER INFORMATION: BNMRP epitope

<400> SEQUENCE: 160

Gln Glu Glu Cys Arg Glu Gln Met Gln Arg Gln Gln Met Leu Ser His
 1               5                  10                  15

Cys Arg Met Tyr Met Arg Gln Gln Met Glu Glu Ser Pro Tyr Gln Thr
            20                  25                  30

Met

<210> SEQ ID NO 161
<211> LENGTH: 110
<212> TYPE: PRT
<213> ORGANISM: Artificial Sequence
<220> FEATURE:
<223> OTHER INFORMATION: BNMRP 12 kD precursor

<400> SEQUENCE: 161

Gln Glu Glu Cys Arg Glu Gln Met Gln Arg Gln Gln Met Leu Ser His
 1               5                  10                  15

Cys Arg Met Tyr Met Arg Gln Gln Met Glu Glu Ser Pro Tyr Gln Thr
```

```
            20                  25                  30
Met Pro Arg Arg Gly Met Glu Pro His Met Ser Glu Cys Cys Glu Gln
        35                  40                  45

Leu Glu Gly Met Asp Glu Ser Cys Arg Cys Gly Leu Arg Met Met
    50                  55                  60

Met Met Arg Met Gln Gln Glu Met Gln Pro Arg Gly Glu Gln Met
65                  70                  75                  80

Arg Arg Met Met Arg Leu Ala Glu Asn Ile Pro Ser Arg Cys His Leu
                85                  90                  95

Ser Pro Met Arg Cys Pro Met Gly Gly Ser Ile Ala Gly Phe
            100                 105                 110

<210> SEQ ID NO 162
<211> LENGTH: 8
<212> TYPE: PRT
<213> ORGANISM: Artificial Sequence
<220> FEATURE:
<223> OTHER INFORMATION: BNMRP epitope

<400> SEQUENCE: 162

Tyr Met Arg Gln Gln Met Glu Glu
1               5

<210> SEQ ID NO 163
<211> LENGTH: 8
<212> TYPE: PRT
<213> ORGANISM: Artificial Sequence
<220> FEATURE:
<223> OTHER INFORMATION: BNMRP epitope

<400> SEQUENCE: 163

Ala Met Arg Gln Gln Met Glu Glu
1               5

<210> SEQ ID NO 164
<211> LENGTH: 8
<212> TYPE: PRT
<213> ORGANISM: Artificial Sequence
<220> FEATURE:
<223> OTHER INFORMATION: BNMRP epitope

<400> SEQUENCE: 164

Tyr Ala Arg Gln Gln Met Glu Glu
1               5

<210> SEQ ID NO 165
<211> LENGTH: 8
<212> TYPE: PRT
<213> ORGANISM: Artificial Sequence
<220> FEATURE:
<223> OTHER INFORMATION: BNMRP epitope

<400> SEQUENCE: 165

Tyr Met Ala Gln Gln Met Glu Glu
1               5

<210> SEQ ID NO 166
<211> LENGTH: 8
<212> TYPE: PRT
<213> ORGANISM: Artificial Sequence
<220> FEATURE:
<223> OTHER INFORMATION: BNMRP epitope

<400> SEQUENCE: 166
```

```
Tyr Met Arg Ala Gln Met Glu Glu
1               5

<210> SEQ ID NO 167
<211> LENGTH: 8
<212> TYPE: PRT
<213> ORGANISM: Artificial Sequence
<220> FEATURE:
<223> OTHER INFORMATION: BNMRP epitope

<400> SEQUENCE: 167

Tyr Met Arg Gln Ala Met Glu Glu
1               5

<210> SEQ ID NO 168
<211> LENGTH: 8
<212> TYPE: PRT
<213> ORGANISM: Artificial Sequence
<220> FEATURE:
<223> OTHER INFORMATION: BNMRP epitope

<400> SEQUENCE: 168

Tyr Met Arg Gln Gln Ala Glu Glu
1               5

<210> SEQ ID NO 169
<211> LENGTH: 7
<212> TYPE: PRT
<213> ORGANISM: Artificial Sequence
<220> FEATURE:
<223> OTHER INFORMATION: BNMRP epitope

<400> SEQUENCE: 169

Asn Leu Ser Pro Met Arg Cys
1               5

<210> SEQ ID NO 170
<211> LENGTH: 7
<212> TYPE: PRT
<213> ORGANISM: Artificial Sequence
<220> FEATURE:
<223> OTHER INFORMATION: BNMRP epitope

<400> SEQUENCE: 170

Asn Leu Ala Pro Met Arg Cys
1               5

<210> SEQ ID NO 171
<211> LENGTH: 7
<212> TYPE: PRT
<213> ORGANISM: Artificial Sequence
<220> FEATURE:
<223> OTHER INFORMATION: BNMRP epitope

<400> SEQUENCE: 171

Asn Leu Ser Ala Met Arg Cys
1               5

<210> SEQ ID NO 172
<211> LENGTH: 7
<212> TYPE: PRT
<213> ORGANISM: Artificial Sequence
<220> FEATURE:
<223> OTHER INFORMATION: BNMRP epitope

<400> SEQUENCE: 172

Asn Leu Ser Pro Ala Arg Cys
```

<210> SEQ ID NO 173
<211> LENGTH: 7
<212> TYPE: PRT
<213> ORGANISM: Artificial Sequence
<220> FEATURE:
<223> OTHER INFORMATION: BNMRP epitope

<400> SEQUENCE: 173

Asn Leu Ser Pro Met Ala Cys
 1               5

<210> SEQ ID NO 174
<211> LENGTH: 7
<212> TYPE: PRT
<213> ORGANISM: Artificial Sequence
<220> FEATURE:
<223> OTHER INFORMATION: BNMRP epitope

<400> SEQUENCE: 174

Asn Leu Ser Pro Met Arg Ala
 1               5

<210> SEQ ID NO 175
<211> LENGTH: 146
<212> TYPE: PRT
<213> ORGANISM: Brazil nut

<400> SEQUENCE: 175

Met Ala Lys Ile Ser Val Ala Ala Ala Leu Leu Val Leu Met Ala
 1               5                  10                  15

Leu Gly His Ala Thr Ala Phe Arg Ala Thr Val Thr Thr Thr Val Val
                20                  25                  30

Glu Glu Glu Asn Gln Glu Glu Cys Arg Glu Gln Met Gln Arg Gln Gln
                35                  40                  45

Met Leu Ser His Cys Arg Met Tyr Met Arg Gln Gln Met Glu Glu Ser
                50                  55                  60

Pro Tyr Gln Thr Met Pro Arg Arg Gly Met Glu Pro His Met Ser Glu
65                  70                  75                  80

Cys Cys Glu Gln Leu Glu Gly Met Asp Glu Ser Cys Arg Cys Glu Gly
                85                  90                  95

Leu Arg Met Met Met Met Arg Met Gln Gln Glu Glu Met Gln Pro Arg
                100                 105                 110

Gly Glu Gln Met Arg Arg Met Met Arg Leu Ala Glu Asn Ile Pro Ser
                115                 120                 125

Arg Cys Asn Leu Ser Pro Met Arg Cys Pro Met Gly Gly Ser Ile Ala
                130                 135                 140

Gly Phe
145

<210> SEQ ID NO 176
<211> LENGTH: 441
<212> TYPE: DNA
<213> ORGANISM: Brazil nut

<400> SEQUENCE: 176
atggcgaaga tttcagttgc ggcagcagcc ctccttgtcc tcatggccct cggccacgcc      60
accgccttcc gggccaccgt caccaccaca gtggtggagg aggagaacca ggaggagtgt     120
cccgagcaga tgcagacaca gcagatgctc agccactgcc ggattaccat gagacagcag     180

-continued

```
atggaggaga gcccgtacca gaccatgccc aggcggggaa tggagccgca catgagcgag    240
tgctgcgagc agctggaggg gatggacgag agctgcagat gcgaaggatt aaggatgatg    300
atgatgagga tgcaacagga ggagatgcaa ccccgagggg agcagatgcg aaggatgatg    360
aggctggccg agaatatccc ttcccgctgc aacctcagtc ctatgagatg ccccatgggt    420
ggctccattg ccgggttctg a                                              441
```

<210> SEQ ID NO 177
<211> LENGTH: 146
<212> TYPE: PRT
<213> ORGANISM: Artificial Sequence
<220> FEATURE:
<223> OTHER INFORMATION: modified BNMRP

<400> SEQUENCE: 177

Met Ala Lys Ile Ser Val Ala Ala Ala Ala Leu Leu Val Leu Met Ala
1               5                   10                  15

Leu Gly His Ala Thr Ala Phe Arg Ala Thr Val Thr Thr Thr Val Val
                20                  25                  30

Glu Glu Glu Asn Gln Glu Glu Cys Ala Glu Gln Met Gln Ala Gln Gln
            35                  40                  45

Met Leu Ser His Cys Ala Met Ala Met Ala Gln Gln Met Glu Glu Ser
        50                  55                  60

Pro Tyr Gln Thr Met Pro Ala Ala Gly Met Glu Pro His Met Ser Glu
65                  70                  75                  80

Cys Cys Glu Gln Leu Glu Gly Met Asp Glu Ser Cys Ala Ala Glu Gly
                85                  90                  95

Leu Met Met Met Met Met Met Ala Gln Glu Met Gln Pro Arg
                100                 105                 110

Gly Glu Gln Met Ala Met Met Met Met Leu Ala Glu Asn Ile Pro Ser
            115                 120                 125

Ala Ala Asn Leu Ser Pro Met Ala Ala Pro Met Gly Gly Ser Ile Ala
        130                 135                 140

Gly Phe
145

The invention claimed is:

1. A method for reducing or eliminating the human IgE-binding activity of a protein comprising SEQ ID NO: 175 having at least one epitope binding to human IgE, comprising modifying the amino acids in the protein to produce a modified protein having the sequence of SEQ ID NO:177, wherein the modified protein exhibits reduced or eliminated IgE binding activity.

* * * * *